US012017002B2

(12) United States Patent
Brambilla et al.

(10) Patent No.: US 12,017,002 B2
(45) Date of Patent: *Jun. 25, 2024

(54) PATIENT INTERFACE WITH INTEGRATED JET PUMP

(71) Applicant: Breathe Technologies, Inc., Irvine, CA (US)

(72) Inventors: Enrico Brambilla, Irvine, CA (US); Samir Ahmad, Irvine, CA (US); Lawrence Mastrovich, Irvine, CA (US); Gary Berman, Irvine, CA (US); David Mastrovich, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 834 days.

This patent is subject to a terminal disclaimer.

(21) Appl. No.: 17/023,018

(22) Filed: Sep. 16, 2020

(65) Prior Publication Data

US 2020/0405986 A1 Dec. 31, 2020

Related U.S. Application Data

(63) Continuation of application No. 15/724,169, filed on Oct. 3, 2017, now Pat. No. 10,792,449.

(51) Int. Cl.
*A61M 16/00* (2006.01)
*A61M 16/06* (2006.01)
(Continued)

(52) U.S. Cl.
CPC .... *A61M 16/0096* (2013.01); *A61M 16/0666* (2013.01); *A61M 16/0672* (2014.02);
(Continued)

(58) Field of Classification Search
CPC ............ A61M 16/0096; A61M 16/127; A61M 16/0666; A61M 16/0672; A61M 16/0816;
(Continued)

(56) References Cited

U.S. PATENT DOCUMENTS 58,051 A 9/1866 Bingham
125,424 A 4/1872 Willcox
(Continued)

FOREIGN PATENT DOCUMENTS

DE 102006023637 A1 11/2007
EP 2473220 A1 7/2012
(Continued)

OTHER PUBLICATIONS

In the United States Patent and Trademark Office, Office Action in re: U.S. Appl. No. 12/578,283, dated Oct. 19, 2011; 5 pages.
(Continued)

*Primary Examiner* — Samchuan C Yao
*Assistant Examiner* — Tina Zhang
(74) *Attorney, Agent, or Firm* — Stetina Brunda Garred & Brucker

(57) ABSTRACT

A patient circuit of a ventilation system, such as a non-invasive open ventilation system, wherein the patient circuit comprises a nasal pillows style patient interface that incorporates at least one "Venturi effect" jet pump proximal to the patient. The patient circuit further comprises a pair of uniquely configured 3-way connectors which, in cooperation with several uniquely configured tri-lumen tubing segments, facilitate the cooperative engagement of the patient interface to a ventilator of the ventilation system.

20 Claims, 9 Drawing Sheets

(51) Int. Cl.
*A61M 16/08* (2006.01)
*A61M 16/10* (2006.01)
*A61M 16/12* (2006.01)

(52) U.S. Cl.
CPC .... *A61M 16/0816* (2013.01); *A61M 16/0833* (2014.02); *A61M 16/0858* (2014.02); *A61M 16/12* (2013.01); *A61M 16/127* (2014.02); *A61M 2016/0027* (2013.01); *A61M 16/0063* (2014.02); *A61M 16/0875* (2013.01); *A61M 16/101* (2014.02); *A61M 2202/0208* (2013.01)

(58) Field of Classification Search
CPC .......... A61M 16/0833; A61M 16/0858; A61M 16/12; A61M 16/0063; A61M 16/0875; A61M 16/101; A61M 2016/0027; A61M 2202/0208; A61M 16/125
See application file for complete search history.

(56) References Cited

U.S. PATENT DOCUMENTS

| | | |
|---|---|---|
| 428,592 A | 5/1890 | Chapman |
| 692,273 A | 2/1902 | Gulick |
| 697,181 A | 4/1902 | Smith |
| 718,785 A | 1/1903 | McNary |
| 778,035 A | 12/1904 | Heltzel |
| 853,439 A | 5/1907 | Clark |
| 859,156 A | 7/1907 | Warnken |
| 909,002 A | 1/1909 | Lambert |
| 1,055,148 A | 3/1913 | Dickson |
| 1,125,542 A | 1/1915 | Humphries |
| 1,125,619 A | 1/1915 | Winchester |
| 1,129,619 A | 2/1915 | Zapf |
| 1,331,297 A | 2/1920 | Walker |
| 1,922,920 A | 8/1933 | Aherne |
| 2,168,705 A | 8/1939 | Charles et al. |
| 2,174,609 A | 10/1939 | Waage |
| 2,178,800 A | 11/1939 | Lombard |
| 2,201,098 A | 5/1940 | McKim |
| 2,259,817 A | 10/1941 | Hawkins |
| 2,338,420 A | 1/1944 | Freitag |
| 2,377,462 A | 6/1945 | Tea et al. |
| 2,499,650 A | 3/1950 | Kaslow |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riu |
| 3,493,703 A | 2/1970 | Finan |
| 3,513,844 A | 5/1970 | Smith |
| 3,581,742 A | 6/1971 | Glenn |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,692,181 A | 9/1972 | Davis |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Jan et al. |
| 4,216,769 A | 8/1980 | Grimes |
| 4,231,363 A | 11/1980 | Grimes |
| 4,231,365 A | 11/1980 | Scarberry |
| 4,248,218 A | 2/1981 | Fischer |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,417,573 A | 11/1983 | De Vries |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,667 A | 3/1985 | Ansite |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |

(56) References Cited

U.S. PATENT DOCUMENTS

| | | | |
|---|---|---|---|
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,708,446 A | 11/1987 | Timmons et al. |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Mcenzi et al. |
| 4,915,103 A | 4/1990 | Nadarasa et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 4,993,862 A | 2/1991 | Pelta |
| 5,000,175 A | 3/1991 | Pue |
| 5,002,050 A | 3/1991 | McGinnis |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,423 A | 10/1991 | Escobal |
| 5,054,484 A | 10/1991 | Hebeler |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | Devires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |

(56) References Cited

U.S. PATENT DOCUMENTS

| | | |
|---|---|---|
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,361 A | 12/1997 | Smith |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,752,511 A | 5/1998 | Simmons et al. |
| 5,762,638 A | 6/1998 | Shikani et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,381 A | 6/1999 | Nord |
| 5,918,597 A | 7/1999 | Jones et al. |
| 5,921,238 A | 7/1999 | Bourdon |
| 5,921,952 A | 7/1999 | Desmond et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Klaus |
| 5,937,853 A | 8/1999 | Stroem |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,279,574 B1 * | 8/2001 | Richardson ....... A61M 16/0096 |
| | | 128/204.17 |
| D449,376 S | 10/2001 | McDonald et al. |
| D449,883 S | 10/2001 | McDonald et al. |
| 6,298,850 B1 | 10/2001 | Argraves |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,340,566 B1 | 1/2002 | McCutchen-Maloney |
| 6,345,619 B1 | 2/2002 | Finn |
| 6,357,060 B2 | 3/2002 | Gloodt |
| 6,357,438 B1 | 3/2002 | Hansen |
| 6,357,440 B1 | 3/2002 | Hansen et al. |
| 6,360,741 B2 | 3/2002 | Truschel |
| 6,367,474 B1 | 4/2002 | Berthon-Jones et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,418,928 B1 | 7/2002 | Bordewick et al. |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,436 B1 | 3/2003 | McGlothen |
| 6,544,192 B2 | 4/2003 | Starr et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,622,726 B1 | 9/2003 | Du |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,644,311 B1 | 11/2003 | Truitt et al. |
| 6,644,315 B2 | 11/2003 | Ziaee |
| 6,651,656 B2 | 11/2003 | Demers et al. |
| 6,655,382 B1 | 12/2003 | Kolobow |
| 6,666,208 B1 | 12/2003 | Schumacher et al. |
| 6,668,828 B1 | 12/2003 | Figley et al. |
| 6,668,829 B2 | 12/2003 | Biondi et al. |

(56) References Cited

U.S. PATENT DOCUMENTS

| | | |
|---|---|---|
| 6,669,712 B1 | 12/2003 | Cardoso |
| 6,675,796 B2 | 1/2004 | McDonald |
| 6,684,883 B1 | 2/2004 | Burns |
| 6,691,702 B2 | 2/2004 | Appel et al. |
| 6,694,973 B1 | 2/2004 | Dunhao et al. |
| 6,694,978 B1 | 2/2004 | Bennarsten |
| 6,705,314 B1 | 3/2004 | O'Dea |
| 6,722,360 B2 | 4/2004 | Doshi |
| 6,742,517 B1 | 6/2004 | Frye et al. |
| 6,752,150 B1 | 6/2004 | Remmers et al. |
| 6,752,151 B2 | 6/2004 | Hill |
| 6,752,152 B2 | 6/2004 | Gale et al. |
| 6,758,217 B1 | 7/2004 | Younes |
| 6,763,832 B1 | 7/2004 | Kirsch et al. |
| 6,769,432 B1 | 8/2004 | Keifer |
| 6,786,953 B2 | 9/2004 | Fornof et al. |
| 6,789,539 B2 | 9/2004 | Martinez |
| 6,796,305 B1 | 9/2004 | Banner et al. |
| 6,807,966 B2 | 10/2004 | Wright |
| 6,810,876 B2 | 11/2004 | Berthon-Jones |
| 6,814,077 B1 | 11/2004 | Eistert |
| 6,837,238 B2 | 1/2005 | McDonald |
| 6,840,240 B1 | 1/2005 | Berthon-Jones et al. |
| 6,848,446 B2 | 2/2005 | Noble |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,510 B2 | 6/2005 | Gale et al. |
| 6,913,601 B2 | 7/2005 | St. Goar et al. |
| 6,920,875 B1 | 7/2005 | Hill et al. |
| 6,920,878 B2 | 7/2005 | Sinderby et al. |
| 6,938,620 B2 | 9/2005 | Payne, Jr. |
| 6,941,950 B2 | 9/2005 | Wilson et al. |
| 6,971,382 B1 | 12/2005 | Corso |
| 6,997,881 B2 | 2/2006 | Green et al. |
| 7,004,170 B1 | 2/2006 | Gillstrom |
| 7,007,692 B2 | 3/2006 | Aylsworth et al. |
| 7,013,892 B2 | 3/2006 | Estes et al. |
| 7,017,575 B2 | 3/2006 | Yagi et al. |
| 7,044,129 B1 | 5/2006 | Truschel et al. |
| 7,047,969 B2 | 5/2006 | Noble |
| 7,059,328 B2 | 6/2006 | Wood |
| 7,077,133 B2 | 7/2006 | Yagi et al. |
| 7,080,646 B2 | 7/2006 | Wiesmann et al. |
| 7,100,609 B2 | 9/2006 | Berthon-Jones et al. |
| 7,121,277 B2 | 10/2006 | Str?m |
| 7,128,578 B2 | 10/2006 | Lampotang et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,189,405 B1 | 3/2007 | Rice et al. |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | B?scher et al. |
| D542,912 S | 5/2007 | Gunaratnam et al. |
| 7,225,811 B2 | 6/2007 | Ruiz et al. |
| 7,237,205 B2 | 6/2007 | Sarel |
| 7,246,620 B2 | 7/2007 | Conroy, Jr. |
| 7,255,103 B2 | 8/2007 | Bassin |
| 7,255,107 B1 | 8/2007 | Gomez |
| 7,267,121 B2 | 9/2007 | Ivri |
| 7,267,123 B2 | 9/2007 | Aylsworth et al. |
| D557,802 S | 12/2007 | Miceli, Jr. et al. |
| 7,302,950 B2 | 12/2007 | Berthon-Jones et al. |
| 7,305,987 B2 | 12/2007 | Sch?ller et al. |
| 7,320,321 B2 | 1/2008 | Pranger et al. |
| 7,328,703 B1 | 2/2008 | Tiep |
| 7,335,181 B2 | 2/2008 | Miller et al. |
| 7,353,826 B2 | 4/2008 | Sleeper et al. |
| 7,373,939 B1 | 5/2008 | DuBois et al. |
| 7,418,965 B2 | 9/2008 | Fukunaga et al. |
| 7,422,015 B2 | 9/2008 | Delisle et al. |
| 7,451,762 B2 | 11/2008 | Chua et al. |
| 7,455,717 B2 | 11/2008 | Sprinkle |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| D588,258 S | 3/2009 | Judson et al. |
| 7,500,482 B2 | 3/2009 | Biederman |
| 7,509,957 B2 | 3/2009 | Duquette et al. |
| D591,419 S | 4/2009 | Chandran et al. |
| 7,516,743 B2 | 4/2009 | Hoffman |
| 7,552,731 B2 | 6/2009 | Jorczak et al. |
| 7,556,038 B2 | 7/2009 | Kirby et al. |
| 7,562,657 B2 | 7/2009 | Blanch et al. |
| 7,588,033 B2 | 9/2009 | Wondka |
| 7,591,265 B2 | 9/2009 | Lee et al. |
| 7,640,934 B2 | 1/2010 | Zollinger et al. |
| 7,658,189 B2 | 2/2010 | Davidson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,845,350 B1 | 12/2010 | Kayyali et al. |
| 7,874,291 B2 | 1/2011 | Ging et al. |
| 7,878,980 B2 | 2/2011 | Ricciardelli |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,905,231 B2 | 3/2011 | Chalvignac |
| 7,913,691 B2 | 3/2011 | Farrugia |
| 7,918,226 B2 | 4/2011 | Acker et al. |
| 7,926,486 B2 | 4/2011 | Childers |
| 7,926,487 B2 | 4/2011 | Drew et al. |
| 7,934,499 B2 | 5/2011 | Berthon-Jones |
| 7,938,114 B2 | 5/2011 | Matthews et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 8,011,365 B2 | 9/2011 | Douglas et al. |
| 8,011,366 B2 | 9/2011 | Knepper |
| 8,015,971 B2 | 9/2011 | Kwok |
| 8,025,052 B2 | 9/2011 | Matthews et al. |
| 8,061,354 B2 | 11/2011 | Schneider et al. |
| 9,199,053 B1 * | 12/2015 | Allum .............. A61M 16/085 |
| 10,792,449 B2 * | 10/2020 | Brambilla ......... A61M 16/0672 |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0092527 A1 | 7/2002 | Wood |
| 2002/0112730 A1 | 8/2002 | Dutkiewicz |
| 2002/0153010 A1 | 10/2002 | Rozenberg et al. |

(56) References Cited

U.S. PATENT DOCUMENTS

| | | |
|---|---|---|
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0121519 A1 | 7/2003 | Estes et al. |
| 2003/0145853 A1 | 8/2003 | Muellner |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0221687 A1 | 12/2003 | Kaigler |
| 2003/0226566 A1 | 12/2003 | Dhuper et al. |
| 2003/0230308 A1 | 12/2003 | Linden |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0206352 A1 | 10/2004 | Conroy, Jr. |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0205098 A1 | 9/2005 | Lampotang et al. |
| 2005/0217668 A1 | 10/2005 | Figley et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0096596 A1 | 5/2006 | Occhialini et al. |
| 2006/0107958 A1 | 5/2006 | Sleeper |
| 2006/0124131 A1 | 6/2006 | Chandran et al. |
| 2006/0124134 A1 | 6/2006 | Wood |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0175473 A1 | 8/2007 | Lewis et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0110462 A1 | 5/2008 | Chekal et al. |
| 2008/0121230 A1 | 5/2008 | Cortez et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178881 A1 | 7/2008 | Whitcher et al. |
| 2008/0178882 A1 | 7/2008 | Christopher et al. |
| 2008/0190429 A1 | 8/2008 | Tatarek |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216841 A1 | 9/2008 | Grimes et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Andis et al. |
| 2009/0101154 A1 | 4/2009 | Mutti et al. |
| 2009/0118632 A1 | 5/2009 | Goepp |
| 2009/0120437 A1 | 5/2009 | Dates et al. |
| 2009/0126739 A1 | 5/2009 | Ng et al. |
| 2009/0133699 A1 | 5/2009 | Nalagatla et al. |
| 2009/0145435 A1 | 6/2009 | White et al. |
| 2009/0151729 A1 | 6/2009 | Judson et al. |
| 2009/0165799 A1 | 7/2009 | Duquette et al. |

(56) References Cited

U.S. PATENT DOCUMENTS

| | | |
|---|---|---|
| 2009/0173347 A1 | 7/2009 | Berthon-Jones |
| 2009/0173349 A1 | 7/2009 | Hernandez et al. |
| 2009/0199855 A1 | 8/2009 | Davenport |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0260629 A1 | 10/2009 | Yee et al. |
| 2009/0277452 A1 | 11/2009 | Lubke et al. |
| 2010/0071693 A1* | 3/2010 | Allum .............. A61M 16/0833 128/205.24 |
| 2010/0071697 A1 | 3/2010 | Jafari et al. |
| 2010/0083968 A1 | 4/2010 | Wondka et al. |
| 2010/0132716 A1 | 6/2010 | Selvarajan et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252044 A1 | 10/2010 | Duquette et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0319703 A1 | 12/2010 | Hayman et al. |
| 2010/0326446 A1 | 12/2010 | Behlmaier |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0041850 A1 | 2/2011 | Vandine et al. |
| 2011/0041855 A1 | 2/2011 | Gunaratnam et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0125052 A1 | 5/2011 | Davenport et al. |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0178419 A1 | 7/2011 | Wood et al. |
| 2011/0180068 A1 | 7/2011 | Kenyon et al. |
| 2011/0214676 A1 | 9/2011 | Allum et al. |
| 2011/0247625 A1 | 10/2011 | Boussignac |
| 2011/0253147 A1 | 10/2011 | Gusky et al. |
| 2011/0265796 A1 | 11/2011 | Amarasinghe et al. |
| 2012/0138050 A1* | 6/2012 | Wondka ............ A61M 16/0057 128/203.14 |
| 2012/0325206 A1* | 12/2012 | Allum .................. A61B 5/097 128/205.24 |
| 2015/0068519 A1 | 3/2015 | Bambrilla et al. |
| 2015/0314098 A1* | 11/2015 | Allum ............... A61M 16/0858 128/207.18 |
| 2017/0209662 A1 | 7/2017 | Ahmad et al. |
| 2019/0099570 A1 | 4/2019 | Brambilla et al. |
| 2019/0232000 A1 | 8/2019 | Allum et al. |

FOREIGN PATENT DOCUMENTS

| | | |
|---|---|---|
| JP | 2009519759 A | 5/2009 |
| WO | 2005018524 A2 | 3/2005 |
| WO | 2006133493 A1 | 12/2006 |
| WO | 2006138580 A2 | 12/2006 |
| WO | 2008019102 A2 | 2/2008 |
| WO | 2008052534 A1 | 5/2008 |
| WO | 2008138040 A1 | 11/2008 |
| WO | 2008144669 A1 | 11/2008 |
| WO | 2009042973 A1 | 4/2009 |
| WO | 2009074160 A1 | 6/2009 |
| WO | 2009082295 A1 | 7/2009 |
| WO | 2009087607 A1 | 7/2009 |
| WO | 2009103288 A1 | 8/2009 |
| WO | 2009109005 A1 | 9/2009 |
| WO | 2009115944 A1 | 9/2009 |
| WO | 2009115948 A1 | 9/2009 |
| WO | 2009115949 A1 | 9/2009 |
| WO | 2009129506 A1 | 10/2009 |
| WO | 2009139647 A1 | 11/2009 |
| WO | 2009149357 A1 | 12/2009 |
| WO | 2009151344 A1 | 12/2009 |
| WO | 2010021556 A1 | 2/2010 |
| WO | 2010022363 A1 | 2/2010 |
| WO | 2010041966 A1 | 4/2010 |
| WO | 2010059049 A2 | 5/2010 |
| WO | 2010060422 A2 | 6/2010 |
| WO | 2010070497 A1 | 6/2010 |
| WO | 2010070498 A1 | 6/2010 |
| WO | 2010115170 A2 | 10/2010 |
| WO | 2010116275 A1 | 10/2010 |
| WO | 2010139014 A1 | 12/2010 |
| WO | 2010150187 A1 | 12/2010 |
| WO | 2011004274 A1 | 1/2011 |
| WO | 2011006199 A1 | 1/2011 |
| WO | 2011014931 A1 | 2/2011 |
| WO | 2011017738 A1 | 2/2011 |
| WO | 2011021978 A1 | 2/2011 |
| WO | 2011022779 A1 | 3/2011 |
| WO | 2011024383 A1 | 3/2011 |
| WO | 2011029074 A1 | 3/2011 |
| WO | 2011035373 A1 | 3/2011 |
| WO | 2011038950 A1 | 4/2011 |
| WO | 2011038951 A1 | 4/2011 |
| WO | 2011044627 A1 | 4/2011 |
| WO | 2011057362 A1 | 5/2011 |
| WO | 2011062510 A1 | 5/2011 |
| WO | 2011086438 A2 | 7/2011 |
| WO | 2011112807 A1 | 9/2011 |
| WO | 2011086438 A3 | 12/2011 |
| WO | 2012106373 A2 | 8/2012 |

OTHER PUBLICATIONS

In the United States Patent and Trademark Office, Office Action in re: U.S. Appl. No. 10/870,849, dated Nov. 16, 2007; 5 pages.

In the United States Patent and Trademark Office, Office Action in re: U.S. Appl. No. 10/922,054, dated May 17, 2006; 5 pages.

In the United States Patent and Trademark Office, Office Action in re: U.S. Appl. No. 11/523,518, dated Dec. 30, 2009; 4 pages.

In the United States Patent and Trademark Office, Office Action in re: U.S. Appl. No. 12/271,484, dated Feb. 9, 2011; 5 pages.

In the United States Patent and Trademark Office, Office Action in re: U.S. Appl. No. 12/754,437, dated Aug. 16, 2011, 5 pages.

In the United States Patent and Trademark Office, Office Action in re: U.S. Appl. No. 11/882,530, dated Apr. 27, 2011; 5 pages.

In the United States Patent and Trademark Office, Restriction Requirement in re: U.S. Appl. No. 12/153,423, dated Oct. 6, 2011; 8 pages.

In the United States Patent and Trademark Office, Restriction Requirement in re: U.S. Appl. No. 14/493,677, dated Aug. 5, 2011, 5 pages.

In the U.S. Patent and Trademark Office, Supplemental Notice of Allowance dated in re: U.S. Appl. No. 10/771,803, dated Dec. 2, 2008, 2 pages.

In the U.S. Patent and Trademark Office, Supplemental Notice of Allowance dated in re: U.S. Appl. No. 10/771,803, dated Nov. 7, 2008, 2 pages.

In the U.S. Patent and Trademark Office, Supplemental Notice of Allowance in re: U.S. Appl. No. 10/870,849, dated Jun. 16, 2009, 2 pages.

(56) References Cited

OTHER PUBLICATIONS

In the U.S. Patent and Trademark Office, Supplemental Notice of Allowance in re: U.S. Appl. No. 11/798,965, dated Aug. 21, 2009, 4 pages.
International Preliminary Report and Written Opinion on Patentability for PCT/DE2004/001646, dated Jul. 3, 2006.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
JP English Translation Office Action, 3 Pages.
JP Office Action, 4 Pages.
Keilty et al., "Effect of inspiratory pressure support on exercise tolerance and breathlessness in patients with severe stable chronic obstructive pulmonary disease," Thorax, 1994, 49(10): 990-994.
Kohnlein et al., "Noninvasive ventilation in pulmonary rehabilitation of COPD patients," Respir. Med., 2009, 103: 1329-1336.
Koska et al., "Evaluation of a Fiberoptic System for Airway Pressure Monitoring," J. Clin. Monit., 1993: 10(4), pp. 247-250.
Lewis, "Breathless No More, Defeating Adult Sleep Apnea," FDA Consumer Magazine, Jun. 1992, pp. 33-37.
Limberg et al., "Changes in Supplemental Oxygen Prescription in Pulmonary Rehabilitation," Resp. Care, 2006:51(11), p. 1302.
MacInryre, "Long-Term Oxygen Therapy: Conference Summary," Resp. Care, 2000: 45(2), pp. 237-245.
MacIntyre et al., "Acute exacerbations and repiratory failure in chronic obstructive pulmonary disease," Proc. Am. Thorac. Soc., 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," Chest, 2003: 123(4), pp. 1112-1118.
McCoy, "Oxygen Conservation Techniques and Devices," Resp. Care, 2000: 45(1), pp. 95-104.

McGinley, "A nasal cannula can be used to treat obstructive sleep apnea"; Am. J. Resp. Crit. Care Med., 2007: 176(2), pp. 194-200.
Menadue et al., "Non-invasive ventilation during arm exercise and ground walking in patients with chronic hypercapnic respiratory failure," Respirology, 2009, 14(2): 251-259.
Menon et al., "Tracheal Perforation. A Complication Associated with Transtracheal Oxygen Therapy," Chest, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," Chest, 1995: vol. 108(2), pp. 509-514.
European Search Report for EP 18 86 4892; dated May 18, 2021.
Polkeyet al., Inspiratory pressure support reduces slowing of inspiratory muscle relations rate during exhaustive treadmill walking in sever COPD, Am. J. Resp. Crit. Care Med., 1996: 154(4, 10), pp. 1146-1150.
Porta et al., Mask proportional assist vs pressure support ventilation in patients in clinically stable condition with chronic venilatory failure, Chest, 2002: 122(2), pp. 479-488.
Prigent et al., Comparative Effects of Two Ventilatory Modes on Speech in Tracheostomized Patients with Neuromuscular Disease, Am. J. Resp. Crit. Care Med., 2003: 167(8), pp. 114-119.
Puente-Maestu et al., Dyspnea, Ventilatory Pattern, and Changes in Dynamic Hyperinflation Related to the Intensity of Constant Work Rate Exercise in COPD, Chest, 2005: 128(2), pp. 651-656.
Ram et al., Non-invasive positive pressure ventilation for treatment of respiratory failure due to exacerbations of chroic obstructive pulmonary disease, Cochrane Database Syst Rev., 2004(3):1-72.
State Intellectual Property Office, 2nd Office Action, Sep. 3, 2014, 15 pages.
Rothe et al., Near Fatal Complication of Transtracheal Oxygen Therapy with the SCOOP(R) System, Pneumologie, 1996: 50(10), pp. 700-702. (English Abstract provided.
Rothfleisch et al., Facilitation of fiberoptic nasotracheal intubation in a morbidly obese patient by simultaneous use of nasal CPAP, Chest, 1994, 106(1): 287-288.
Sanders et al., CPAP Via Nasal Mask: A Treatment for Occlusive Sleep Apnea, Chest, 1983: 83(1), pp. 144-145.
Sinderby et al., Neural control of mechanical ventilation in respiratory failure, Nat. Med., 1999: 5(12), pp. 1433-1436.
Somfay et al., Dose-Response Effect of Oxygen on Hyperinflation and Exercise Endurance in Nonhypoxaemic COPD Patients, Eur. Resp. J., 2001: 18, pp. 77-84.
Sullivan et al., Reversal of Obstructive Sleep Apnoea by Continuous Positive Airway Pressure Applied Through the Nares, The Lancet, 1981: 1(8225), pp. 862-865.
Tiep et al., Pulsed nasal and transtracheal oxygen delivery, Chest, 1990: 97, pp. 364-368.
Tsuboi et al., Ventilatory Support During Exercise in Patients With Pulmonary Tuberculosis Sequelae, Chest, 1997: 112(4), pp. 1000-1007.
VHA/DOD Clinical Practice Guideline, Management of Chronic Obstructive Pulmonary Disease, Aug. 1999, Ver. 1.1a, Updated Nov. 1999.
Walsh, McGraw Hill Pocket reference Machinists' and Metalworker' Pocket Reference, New York McGraw-.
Wijkstra et al., Nocturnal non-invasive positive pressure ventilation for stable chronic obstructive pulmonary disease, Cochrane Database Syst. Rev., 2002, 3: 1-22.
Yaeger et al., Oxygen Therapy Using Pulse and Continuous Flow With a Transtracheal Catheter and a Nasal Cannula, Chest, 1994: 106, pp. 854-860.
"AARC Clinical Practice Guideline: Oxygen Therapy in the Home or Extended Care Facility," Resp. Care, 1992: 37(8), pp. 918-922.
"ATS Statement: Guidelines for the Six-Minute Walk Test," Am. J. Respir. Crit. Care Med., 2002: 166, pp. 111-117.
"Jet 1". Collins English Dictionary. http://search.credoreference.com/content/entry/hcengdict/jet-1/0 (May 4, 2014).

(56) References Cited

OTHER PUBLICATIONS

AU Patent Examination Report, Sep. 6, 2013, 3 Pages, Brisbane Australia.
CN English Translation Office Action, 15 Pages.
CN Office Action, 15 Pages.
European patent Office Search Report issued Oct. 19, 2007 in co-pending EP 04762494.
In the U.S. Patent and Trademark Office, Ex Parte Quayle Office Action in re: U.S. Appl. No. 29/388,700, dated Oct. 7, 2011, 5 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 10/922,054, dated Nov. 27, 2007, 9 pages.
In the U.S. Patent and Trademark Office, Final Office Action in re: U.S. Appl. No. 11/523,519, dated Nov. 26, 2007, 14 pages.
In the U.S. Patent and Trademark Office, Final Office Action in re: U.S. Appl. No. 11/798,965, dated Apr. 9, 2009, 6 pages.
In the U.S. Patent and Trademark Office, Non-Final Office Action dated in re: U.S. Appl. No. 10/567,746, dated Oct. 5, 2009, 9 pages.
In the United States Patent and Trademark Office, Notice of Allowance and Examiner's Interview Summary in re: U.S. Appl. No. 11/523,519, dated Jan. 16, 2009; 10 pages.
In the United States Patent and Trademark Office, Notice of Allowance and Examiner's Interview Summary in re: U.S. Appl. No. 12/076,062, dated Nov. 2, 2011; 8 pages.
In the United States Patent and Trademark Office, Notice of Allowance in re: U.S. Appl. No. 10/870,849, dated Jun. 3, 2009; 4 pages.
In the United States Patent and Trademark Office, Notice of Allowance in re: U.S. Appl. No. 10/870,849, dated May 14, 2009; 8 pages.
In the United States Patent and Trademark Office, Notice of Allowance in re: U.S. Appl. No. 10/922,054, dated Feb. 12, 2008; 6 pages.
In the United States Patent and Trademark Office, Notice of Allowance in re: U.S. Appl. No. 11/798,965, dated Jul. 17, 2009.
In the United States Patent and Trademark Office, Office Action in re: U.S. Appl. No. 10/771,803, dated Jun. 14, 2017; 12 pages.
In the United States Patent and Trademark Office, Office Action in re: U.S. Appl. No. 10/870,849, dated Feb. 22, 2007; 13 pages.
In the United States Patent and Trademark Office, Office Action in re: U.S. Appl. No. 10/922,054, dated Mar. 14, 2007; 14 pages.
In the United States Patent and Trademark Office, Office Action in re: U.S. Appl. No. 10/922,054, dated Sep. 7, 2006, 21 pages.
In the United States Patent and Trademark Office, Office Action in re: U.S. Appl. No. 11/523,519, dated Jul. 11, 2008; 13 pages.
In the United States Patent and Trademark Office, Office Action in re: U.S. Appl. No. 11/523,519, dated Mar. 7, 2007; 11 pages.
In the United States Patent and Trademark Office, Office Action in re: U.S. Appl. No. 11/798,965, dated Jul. 29, 2008; 12 pages.
In the United States Patent and Trademark Office, Office Action in re: U.S. Appl. No. 12/076,062, dated Jan. 13, 2011; 14 pages.
In the United States Patent and Trademark Office, Office Action in re: U.S. Appl. No. 12/355,753, dated Sep. 28, 2011; 32 pages.
AU Office Action, 112 Pages.

Ambrosino, Exercise and noninvasive ventilatory support, Monaldi Arch Chest Dis., 2000: 55(3): 242-246.
Ambrosino, Weaning and Respiratory Muscle Dysfunction: The Egg Chicken Dilemma, Chest, 2005: 128(2), pp. 481-483.
Bach et al., Intermittent Positive Pressure Ventilation via Nasal Access in the Management of Respiratory Insufficiency, Chest, 1987: 92(1), pp. 168-170.
Banner et al., Imposed Work of Breathing and Methods of Triggering a Demand-Flow, Continuous Positive Airway Pressure System, Critical Care Medicine, 1993: 21(2), pp. 183-190.
Banner et al., Site of Pressure Measurement During Spontaneous Breathing with Continuous Positive Airway Pressure: Effect on Calculating Imposed Work of Breathing, Critical Care Medicine, 1992: 20(4), pp. 528-533.
Banner et al., Extubating at a Pressure Support Ventilation Level Corresponding to Zero Imposed Work of Breathing, Anesthesiology, Sep. 1994: 81(3, A), p.
Barakat et al., Effect of noninvasive ventilatory support during exercise of a program in pulmonary rehabilitation in patients with COPD, Int. J. Chron. Obstruct. Pulmon. Dis., 2007: 2(4), pp. 585-591.
Barreiro et al., Noninvasive ventilation, Crit Care Clin., 2007; 23(2): 201-22.
Bauer et al., ADAM Nasal CPAP Circuit Adaptation: A Case Report, Sleep, 1991: 14(3), pp. 272-273.
Blanch, Clinical Studies of Tracheal Gas Insufflation, Resp. Care, 2001: 45(2), pp. 158-166.
Borghi-Silva et al., Non-invasive ventilation improves peripheral oxygen saturation and reduces fatigability of quadriceps in patients with COPD, Respirology, 2009, 14:537-546.
Bossi et al., Continuous Positive Airway Pressure in the Spontaneously Breathing Newborn by Means of Bilateral Nasal Cannulation, Monatsschr Kinderheilkd, 1975: 123(4), pp. 141-146.
Boussarsar et al., Relationship between ventilatory settings and barotrauma in the acute respiratory distress syndrome, Intensive Care Med., 2002: 28(4): 406-13.
Chang et al., Reduced Inspiratory Muscle Endurance Following Successful Weaning From Prolonged Mechanical Ventilation, Chest, 2005: 128(2), pp. 553-559.
Charlotte Regional Medical Center, Application of the Passy-Muir Tracheostomy and Ventilator, Speech-Language Pathology Department, Jan. 1995, 8 pages.
Christopher et al., Preliminary Observations of Transtracheal Augmented Ventilation for Chronic Severe Respiratory Disease, Resp. Care, 2001: 46(1), pp. 15-25.
Christopher, et al., Transtracheal Oxygen Therapy for Refractory Hypoxemia, JAMA, 1986: 256(4), pp. 494-497.
Ciccolella et al.;, Administration of High-Flow, Vapor-phased, Humidified Nasal Cannula Air (HF-HNC) Decreases Work of Breathing (WOB) in Healthy Subjects During Exercise, AmJRCCM, Apr. 2001: 163(5), Part 2, pp. A622. (Abstract Only).
Clini et al., The Italian multicentre study on noninvasive ventilation in chronic obstructive pulmonary disease patients, Eur. Respir. J., 2002, 20(3): 529-538.
Costa et al., Influence of noninvasive ventilation, BiPAP on exercise tolerance and respiratory muscle strength.
Canadian Office Action for CA Application No. 2,757,588, mailed on Dec. 4, 2015.
Diaz et al., Breathing Pattern and Gas Exchange at Peak Exercise in COPD Patients With and Without Tidal Flow Limitation at Rest, European Respiratory Journal, 2001: 17, pp. 1120-1127.
English Translation, JP Final Decision of Rejection for Patent Application No. 2012-503761.
Enright, The six-minute walk test, Resp. Care, 2003: 8, pp. 783-785.
Ferreira et al., Trigger Performance of Mid-level ICU Mechanical Ventilators During Assisted Ventilation: A Bench Study, Intensive Care Medicine, 2008;34:1669-1675.
Fink, Helium-Oxygen: An Old Therapy Creates New Interest, J. Resp. Care. Pract. now RT for Decision Makers in Respiratory Care, 1999, pp. 71-76.
Gaughan et al., A Comparison in a Lung Model of Low- and High-Flow Regulators for Transtracheal Jet Ventilation, Anesthesiology, 1992: 77(1), pp. 189-199.

(56) References Cited

OTHER PUBLICATIONS

Gregoretti, et al., Transtracheal Open Ventilation in Acute Respiratory Failure Secondary to Severe Chronic Obstructive Pulmonary Disease Exacerbation, Am. J. Resp. Crit. Care. Med., 2006: 173(8), pp. 877-881.
Haenel et al., Efficacy of Selective Intrabronchial Air Insufflation in Acute Lobar Colapse, Am. J. Surg., 1992: 164(5), pp. 501-505.
Mettey, Use of CPAP Nasal Cannula for Aids of the Newborns in Tropical Countries, Medecine Tropicale, 1985: 45(1), pp. 87-90.
Nahmias et al., Treatment of the Obstructive Sleep Apnea Syndrome Using a Nasopharyngeal Tube, Chest, 1988:94(6), pp. 1142-1147.
Nava et al., Non-invasive ventilation, Minerva Anestesiol., 2009: 75(1-2), pp. 31-36.
Office Action, Sep. 3, 2014, 15 pages.
Passy-Muir Inc., Clinical Inservice Outline, Apr. 2004, 19 pages.
Peters et al., Combined Physiological Effects of Bronchodilators and Hyperoxia on Exertional Dyspnea in Normoxic COPD, Thorax, 2006: 61, pp. 559-567.

\* cited by examiner

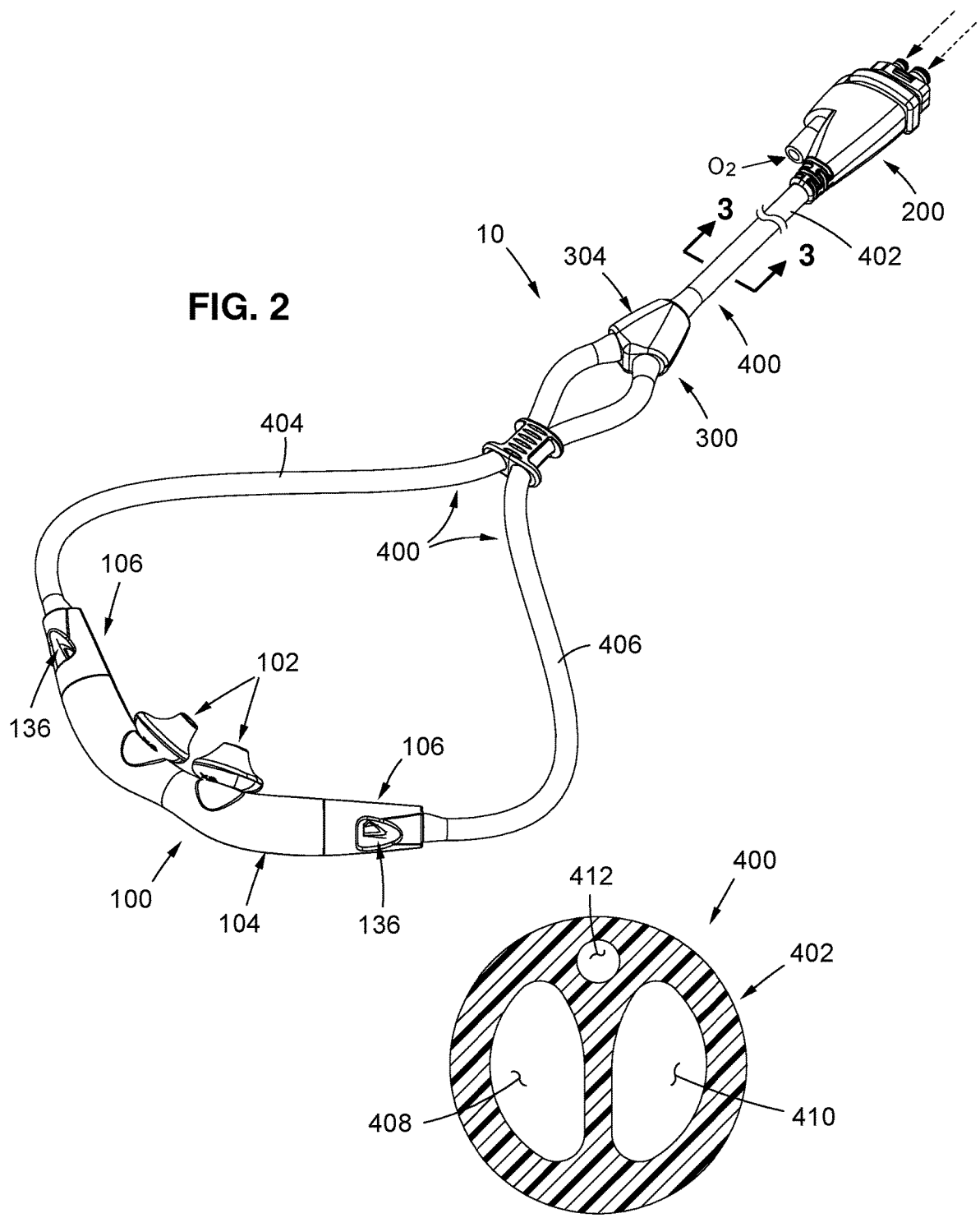

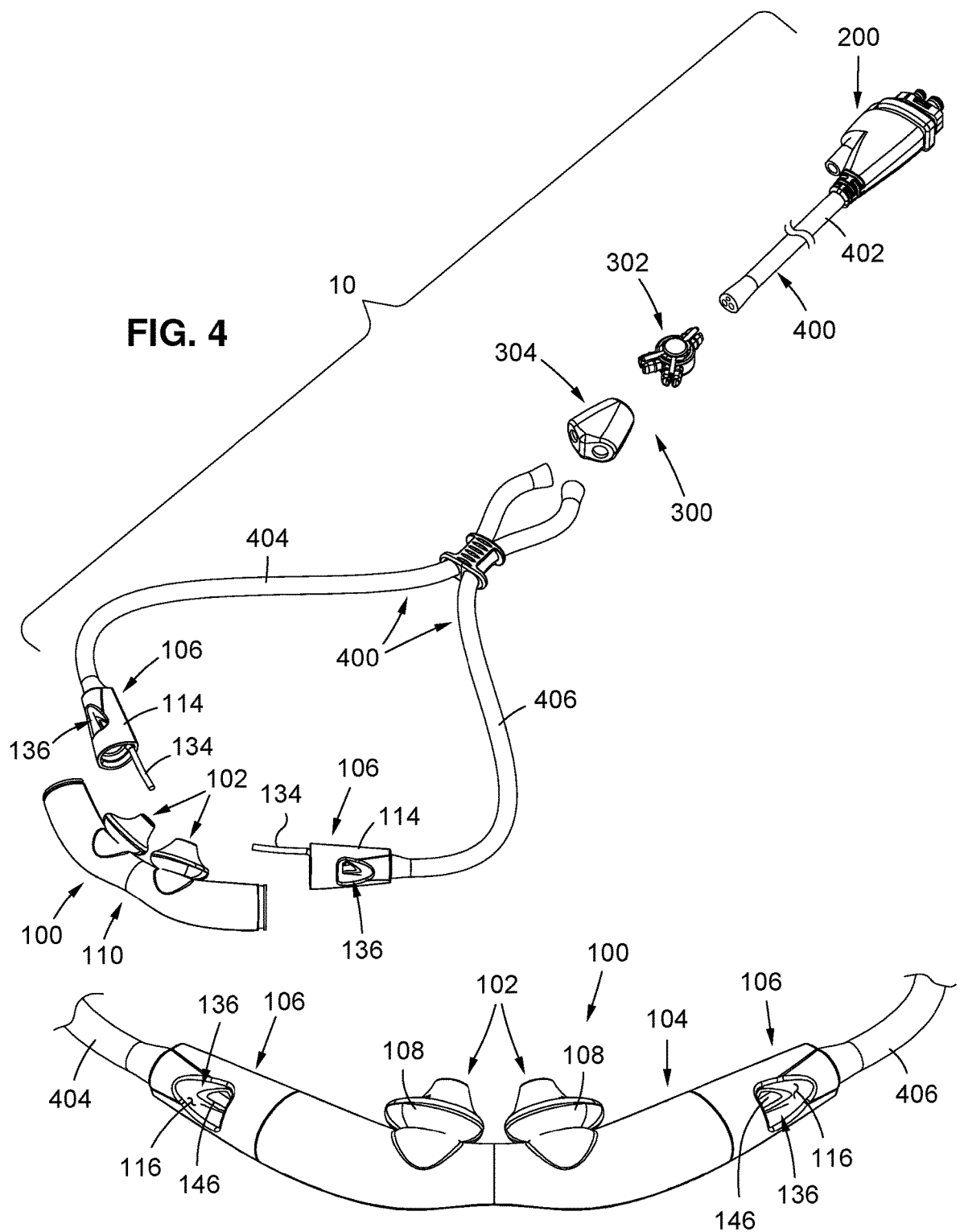

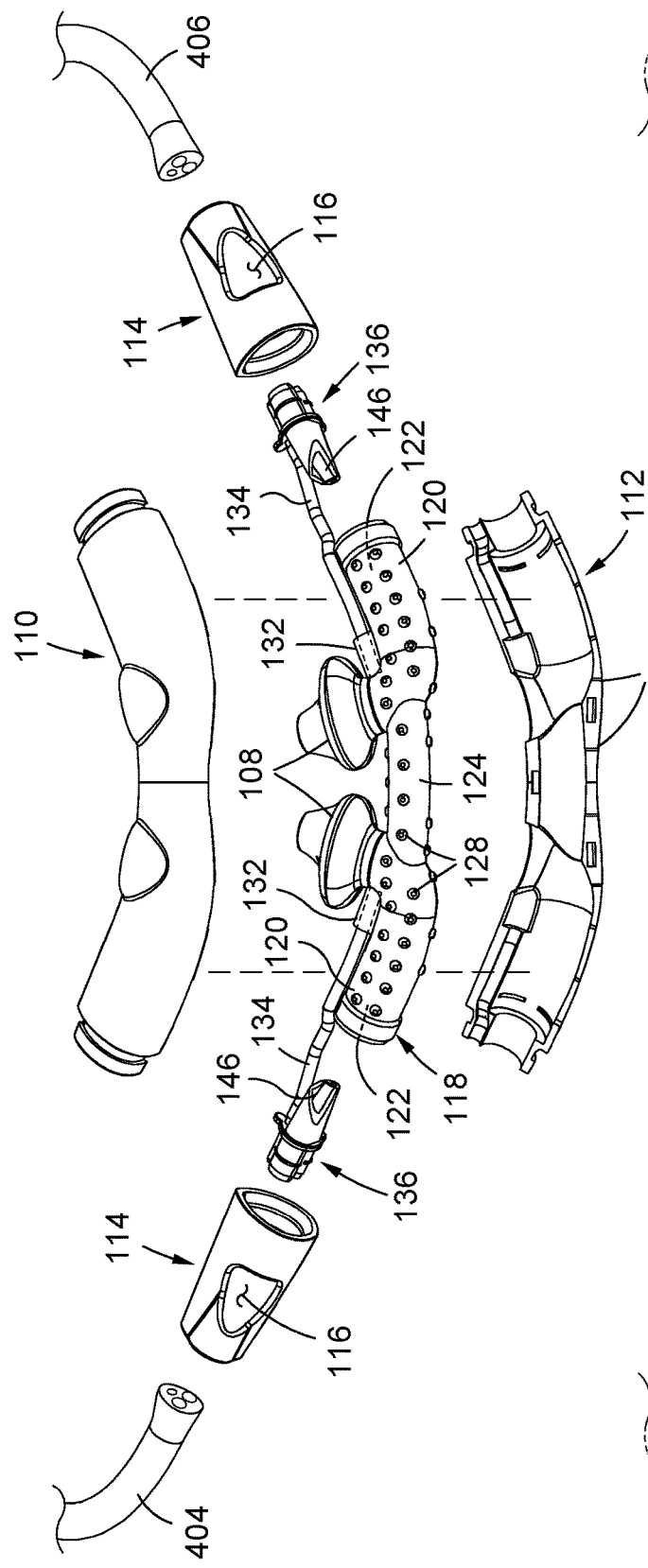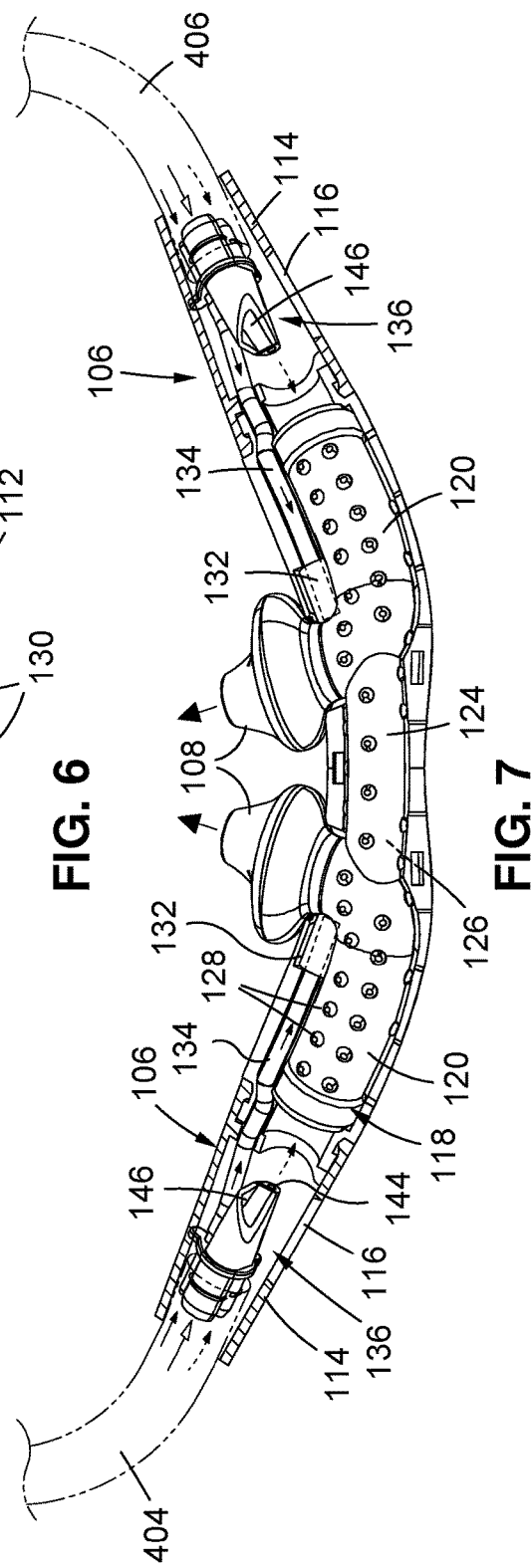
FIG. 6
FIG. 7

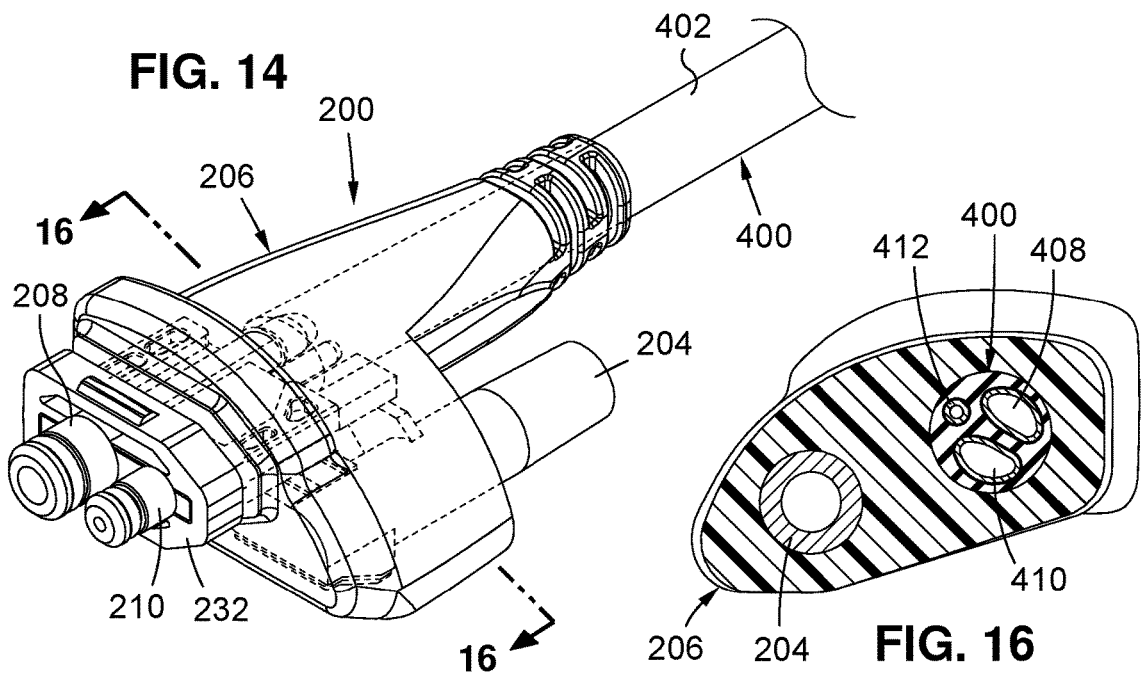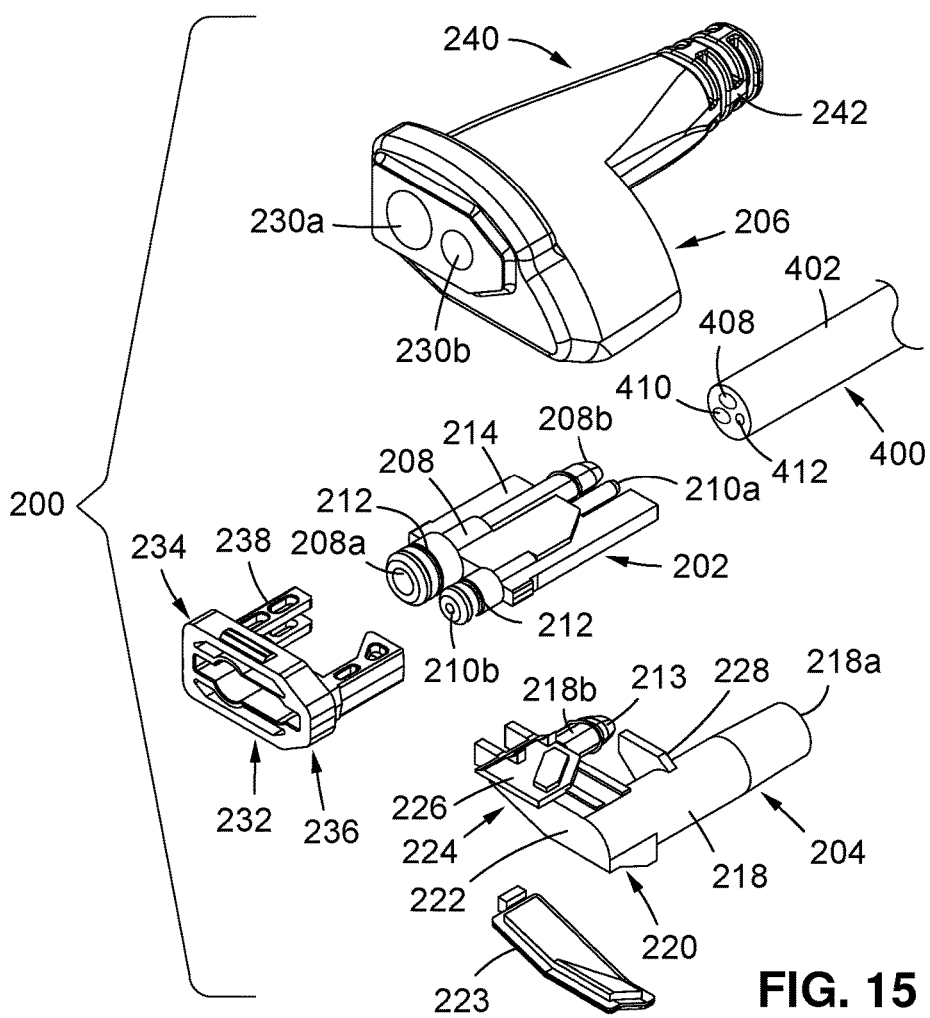

PATIENT INTERFACE WITH INTEGRATED JET PUMP

CROSS-REFERENCE TO RELATED APPLICATIONS

This application is a continuation of U.S. patent application Ser. No. 15/724,169, filed Oct. 3, 2017 and entitled "PATIENT INTERFACE WITH INTEGRATED JET PUMP," the entire disclosure of which is hereby wholly incorporated by reference.

STATEMENT RE: FEDERALLY SPONSORED RESEARCH/DEVELOPMENT

Not Applicable

BACKGROUND

1. Field of the Invention

The present disclosure relates to systems and methods for controlling delivery of a pressurized flow of breathable gas to a patient and, more particularly, to a patient circuit of a ventilation system, such as a non-invasive open ventilation system, wherein the patient circuit comprises a nasal pillows style patient interface that incorporates at least one "Venturi effect" jet pump proximal to the patient, the patient circuit further comprising a pair of uniquely configured 3-way connectors which, in cooperation with several uniquely configured tri-lumen tubing segments, facilitate the cooperative engagement of the patient interface to a ventilator of the ventilation system.

2. Description of the Related Art

As is known in the medical arts, mechanical ventilators comprise medical devices that either perform or supplement breathing for patients. The vast majority of contemporary ventilators use positive pressure to deliver gas to the patient's lungs via a patient circuit between the ventilator and the patient. The patient circuit typically consists of one or two large bore tubes that interface to the ventilator on one end, and a patient mask on the other end. In many instances, the patient mask is not provided as part of the ventilation system, and a wide variety of patient masks can be used with any ventilator.

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

With particular regard to vented patient circuits, these are used only to carry gas flow from the ventilator to the patient and patient mask, and require a patient mask with vent openings. When utilizing vented circuits, the patient inspires fresh gas from the patient circuit, and expires $CO_2$-enriched gas, which is typically purged from the system through the vent openings in the mask. In the vented patient circuit, the ventilator pressurizes the gas to be delivered to the patient inside the ventilator to the intended patient pressure, and then delivers that pressure to the patient through the patient circuit. Very small pressure drops develop through the patient circuit due to gas flow though the small amount of resistance created by the tubing. Some ventilators compensate for this small pressure drop either by mathematical algorithms, or by sensing the tubing pressure more proximal to the patient.

One notable deficiency of certain prior art ventilation systems is that when the breathable gas supplied to the ventilator is air, the ventilator and patient circuit (including the patient interface) of the ventilation system are not well suited for delivering supplemental oxygen to the patient from an oxygen concentrator. Along these lines, it is known that the maximum outlet from a stationary oxygen concentrator is around 5 l/min of oxygen and 10-15 PSI, whereas certain existing ventilators require a minimum of 42 PSI to operate correctly and may require up to 40-45 l/min peak flow to ventilate a patient, depending on the therapy. The present invention, as will be described in more detail below, provides an innovative patient circuit for addressing this deficiency in the prior art.

BRIEF SUMMARY

In accordance with the present disclosure, there is provided a patient circuit of a ventilation system. When used in conjunction with a ventilation system wherein the compressor of such system pressurizes air to the values of pressure and flow compatible with the requirement for the gas supplied to the ventilator of the same system, the patient circuit is adapted administer the therapy to the patient, and to allow for supplemental oxygen coming from an oxygen concentrator to be delivered to a dedicated port in the patient circuit, and delivered to the patient via the patient interface. Along these lines, the design of the patient circuit makes it possible to deliver low pressure/low flow oxygen coming from an oxygen concentrator bypassing the compressor and the ventilator of the ventilation system, and thus avoiding safety problems related to the pressurization of oxygen in a compressor, or calibration problems related to the flow sensing calibration of the ventilator when delivering mixtures of oxygen and air.

The patient interface comprises four (4) primary features. The first of these is a nasal pillows style patient interface that incorporates at least one "Venturi effect" jet pump proximal to the patient. This patient interface has several unique design features. One is the aforementioned Venturi-effect jet pumps that convert and multiply high pressure/low flow breathable gas delivered by the ventilator into high flow/low pressure gas for the patient. The low-pressure oxygen delivery nozzle associated with each of the jet pumps is designed in a way that the positive pressure created during the delivery of the highest acceptable oxygen flow (i.e., 5 l/min) is not more than 0.5 cmH2O. Stated another way, such nozzle is effectively designed to be a very inefficient jet pump so that any delivered flow will not interfere with the proper operation of the corresponding high-pressure jet pump. This is achieved by keeping a large cross-sectional area of the nozzle, thus having a very low flow velocity and virtually no entrainment potential. The patient interface is also adapted to facilitate open ventilation, i.e., the entrainment ports of the jet pumps are open to ambient and the patient can spontaneously breathe, if capable of doing so, in case of failure of the ventilator of the ventilation system. Further, the patient interface is configured to achieve minimal obtrusiveness, and looks similar to an oxygen cannula though behaving like patient interfaces for ventilators that are normally more obtrusive than an oxygen cannula.

Another feature of the patient interface is a three-way primary connector that is configured to be placed into fluid communication with the ventilator alone or in combination with the compressor. The primary connector may also optionally be placed into fluid communication with an oxygen concentrator via a dedicated low-pressure oxygen port, or via the ventilator to another oxygen source such as an oxygen canister or wall connection in substitution for the compressor. Along these lines, the primary connector defines a high-pressure air/oxygen port for high pressure air or for oxygen emanating from the ventilator, the above-described low-pressure oxygen port for supplemental oxygen from an oxygen concentrator, and a pressure sensing port which is also placeable into fluid communication with the ventilator, the high-pressure air/oxygen, low-pressure oxygen and pressure sensing ports all being fluidly isolated from each other within the primary connector. The primary connector, when facilitating the delivery of supplemental oxygen from an oxygen concentrator through the use of the oxygen port, allows for such supplemental oxygen delivery to the patient via the other features of the patient circuit (and notably the patient interface) while bypassing the compressor and the ventilator of the ventilation system for the reasons set forth above. When facilitating the delivery of oxygen from an oxygen canister or wall connection to the patient via the ventilator and other features of the patient circuit, such canister or wall connection is effectively substituted for the compressor, thus again avoiding any safety problems related to the pressurization of oxygen in a compressor.

A further feature of the patient interface is a three-way wye connector that is fluidly connectible to the primary connector. The wye connector is uniquely configured to effectively bifurcate three (3) separate and distinct flow paths for high pressure air or oxygen flow, low pressure oxygen flow, and the pressure sensing, into two sets of those three paths, each such set being adapted to for placement into for effective fluid commination to respective ones of opposed end portions of the patient interface.

A final feature of the patient interface is tri-lumen tubing, which is provided in at least three (3) separate and distinct segments. One such segments is used to facilitate the fluid communication between the primary connector and the wye connector, with the remaining two segments being used to facilitate the fluid communication between the wye connector and respective ones of the opposed end portions of the patient interface. The tubing is about 5.5 mm in diameter and, within the patient circuit, is routed around the ears of the patient. A normal ventilator interface for adults usually requires one or two 22 mm diameter tubes, depending on the therapy, that are connected to the front of the interface. Along these lines, each segment of the tri-lumen tubing defines a high-pressure air/oxygen lumen for high pressure air emanating from the ventilator/compressor or for oxygen emanating from the ventilator alone, a low-pressure oxygen lumen for supplemental oxygen emanating from an oxygen concentrator, and a pressure sensing lumen, all of these lumens being fluidly isolated from each other.

In the patient circuit of the present disclosure, it is contemplated that the additional oxygen port of the primary connector, along with the low-pressure oxygen lumens of the tri-lumen tubing, can be used for the delivery of gasses other than supplemental oxygen to the patient interface, if needed by the therapy as prescribed by a doctor, and can also be used to deliver high humidity gas to deliver additional humidification to the patient via the patient interface.

Thus, the patient circuit of the present disclosure is capable of accommodating multiple configurations of the ventilation system. These configurations include: 1) placing the patient interface (and hence the patient wearing the same) into fluid communication with high-pressure air emanating from the compressor and ventilator; 2) placing the patient interface into fluid communication with high-pressure air emanating from the compressor and ventilator, but also with supplemental low-pressure oxygen supplied from an oxygen concentrator and bypassing the compressor and ventilator; 3) placing the patient interface into fluid communication with oxygen emanating from a canister or wall connection via the ventilator (with the compressor being removed from the ventilation system) and further with oxygen emanating from an oxygen concentrator, the patient being ventilated with oxygen and also receiving additional oxygen from the concentrator; 4) placing the patient interface into fluid communication with oxygen emanating from a canister or wall connection via the ventilator (with the compressor and the oxygen concentrator being removed from the ventilation system); and 5) placing the patient interface into fluid communication with oxygen emanating from a canister or wall connection via the ventilator (with the compressor and the oxygen concentrator being removed from the ventilation system), with the low-pressure oxygen port of the primary connector of the patient circuit being connected to the low pressure port of the regulator used with the canister to allow the patient will be ventilated with oxygen while also receiving additional oxygen from the same gas source, i.e., the canister.

It is contemplated that various components can be added to the existing design in the form of an additional oxygen delivery line and delivery nozzles. In greater detail, one possible alternative embodiment is to have an oxygen connector, compatible with 6 mm oxygen cannula connectors, that can be glued or clipped over the wye connector of the patient interface. From there, a single tube can deliver oxygen to one or a pair of delivery nozzles that can be glued or clipped in place over or around one entrainment area or respective ones of the entrainment areas of the patient interface. In other words, the oxygen line may deliver gas to one delivery nozzle, and be extended to deliver the gas to another delivery nozzle located on the other side of the patient interface, which is clipped or glued in place near or over the other entrainment area. Because the oxygen delivery nozzles are connected in series, this arrangement requires that the holes of the nozzles and the cross section of the tubes be balanced in a way to ensure the same amount of oxygen flow is delivered by both nozzles.

A further alternative arrangement is to have the two nozzles connected in parallel, so that two tubes depart from the oxygen connector secured on the wye connector of the patient interface. This configuration is easier to pneumatically balance, though having additional tubing over both the right and left side on the bi-lumen tubing segments (in substitution for the tri-lumen tubing segments) used to facilitate high pressure air/oxygen delivery and pressure sensing in the patient circuit. The clip-on or glue-on nozzles are designed in a way to minimize the occlusion of the entrainment ports, so that the inspiratory and expiratory resistance values of the patient interface can be retained unaltered. The delivery nozzles are also positioned in a way such that the oxygen flow is delivered in the zone between the nozzle and the throat of the jet pump. This position is considered optimal to minimize any positive pressure created by the oxygen flow and to maximize the amount of oxygen that is entrained and delivered to the patient. Clips and a modified cinch can also be included in the design to help manage the tubes around the patients' face. The small tube connecting the left and right oxygen nozzles in the series configuration is designed in a way that its presence does not interfere with the pillows of the patient interface.

The present invention is best understood by reference to the following detailed description when read in conjunction with the accompanying drawings.

BRIEF DESCRIPTION OF THE DRAWINGS

These, as well as other features of the present disclosure, will become more apparent upon reference to the drawings wherein:

FIG. 2 is a top perspective view of the patient circuit constructed in accordance with the present disclosure;

FIG. 3 is a cross-sectional view of one of the three segments of tri-lumen tubing included in the patient circuit, taken along line 3-3 of FIG. 2;

FIG. 4 is an exploded view of the patient circuit shown in FIG. 2;

FIG. 5 is a front elevational view of the patient interface included in the patient circuit;

FIG. 6 is an exploded view of the patient interface shown in FIG. 5;

FIG. 7 is a cross-sectional view of the patient circuit shown in FIG. 5;

FIG. 14 is a top perspective view of the primary connector of the patient circuit;

FIG. 15 is an exploded view of the primary connector shown in FIG. 14;

FIG. 16 is a cross-sectional view taken along line 16-16 of FIG. 14;

Common reference numerals are used throughout the drawings and detailed description to indicate like elements.

DETAILED DESCRIPTION

Figure 1:
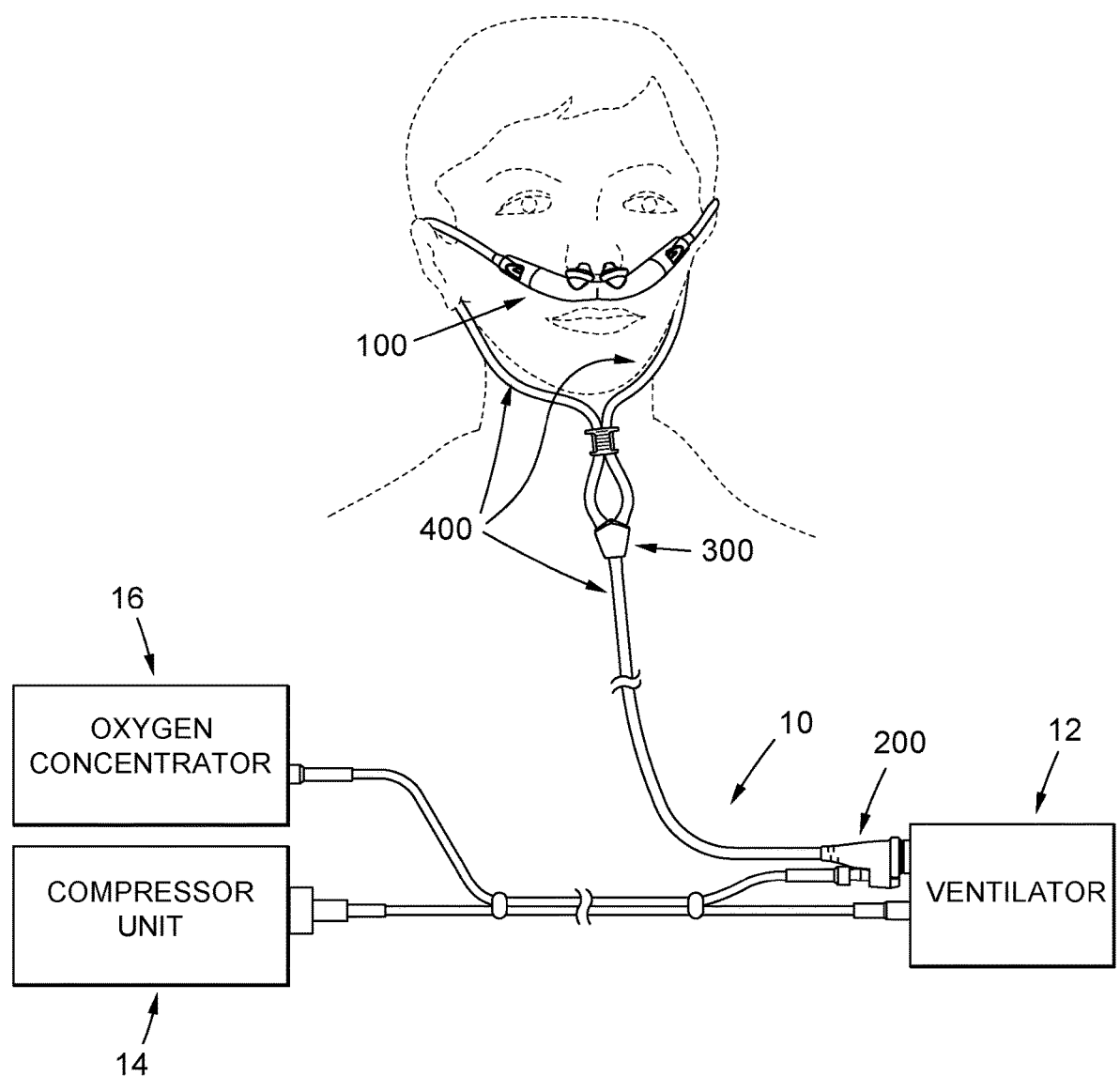
FIG. 1 is a schematic depiction of the patient circuit constructed in accordance with the present disclosure.

Referring now to the drawings wherein the showings are for purposes of illustrating various embodiments of the present disclosure only, and not for purposes of limiting the same, FIG. 1 provides a schematic representation of the patient circuit 10 constructed in accordance with the present disclosure. The patient circuit 10 is particularly suited for use in conjunction with the ventilation system described with particularity in Applicant's U.S. Patent Publication No. 2017/0209662 A1 published Jul. 27, 2017, the entire disclosure of which is incorporated herein by reference. As described in that published document, the modular ventilation system is capable of transitioning between a stationary configuration, an extended range configuration, and a stand-alone configuration, with corresponding methods of use providing continuous or intermittent ventilatory support for the care of individuals who require mechanical ventilation. Such modular ventilation system is primarily composed of a ventilator 12, a compressor unit 14, and a patient interface which, for purposes of the subject application and for consistency with the further description below, is labeled in FIG. 1 with the reference number 100.

As indicated above, the ventilation system comprising the ventilator 12, compressor unit 14, and patient circuit 10 (including the patient interface 100) may be used in at least three different configurations, including a stationary configuration, an extended range configuration, and a stand-alone configuration. In the stationary configuration, the ventilator 12 is docked with the compressor unit 14, with the patient circuit 10 (and hence the patient interface 100) being connected to the ventilator 12 (or to the ventilator 12 via the compressor unit 14) for ventilation of a stationary patient. In the extended range configuration, which may enable the patient to engage in localized daily living activities, the ventilator 12 is not docked with the compressor unit 14, but instead is near the patient, where it receives compressed air from the compressor of the compressor unit 14 via a compressed gas supply hose, with the patient circuit 10 connected to the ventilator 12. In the stand-alone configuration, which may enable the patient to engage in non-localized activities, the ventilator 12 is not docked or otherwise connected with the compressor unit 14, but instead is connected to and receives compressed gas from an external compressed gas source such as an oxygen or air cylinder, or hospital wall source, with the patient circuit 10 being connected to the ventilator 12. In either of the stationary, stand-alone or extended configurations, the patient circuit 10 may also receive low-pressure oxygen which supplements the high-pressure air delivery from an oxygen source, such as an oxygen concentrator 16.

In general terms, the patient circuit 10 comprises four (4) primary features. These are: 1) a nasal pillows style patient 100 interface that incorporates at least one "Venturi effect" jet pump proximal to the patient; 2) a three-way primary connector 200 that is configured to be placed into fluid communication with (i) a ventilator/compressor combination to facilitate the delivery of high pressure air, (ii) a ventilator/compressor combination and to an oxygen concentrator to facilitate the delivery of high pressure air in combination with supplemental low-pressure oxygen bypassing the compressor/ventilator, (iii) an oxygen a canister or wall connection via a ventilator (with the compressor being removed from the ventilation system) and further with an oxygen concentrator to allow for patient ventilation with oxygen and also with additional oxygen from the concentrator, (iv) an oxygen canister or wall connection via a ventilator (with the compressor and the oxygen concentrator being removed from the ventilation system) to facilitate the delivery of oxygen from the canister or wall connection; and (v) an oxygen canister or wall connection via the ventilator (with the compressor and the oxygen concentrator being removed from the ventilation system) and to the low pressure port of the regulator used with the canister to allow for the patient ventilation with oxygen while also receiving additional oxygen from the same gas source; 3) a three-way wye connector 300 that is fluidly connectible to the primary connector 200 and is configured to effectively bifurcate three (3) separate and distinct flow paths for high pressure air or oxygen flow, low pressure oxygen flow, and the pressure sensing, into two sets of those three paths, each such set being adapted to for placement into for effective fluid commination to respective ones of opposed end portions of the patient interface 100; and 4) tri-lumen tubing 400, which is provided in at least three (3) separate and distinct segments, one of which is used to facilitate the fluid communication between the primary connector 200 and the wye connector 300, with the remaining two segments being used to facilitate the fluid communication between the wye connector 300 and respective ones of the opposed end portions of the patient interface 100. For purposed of clarity, the structural and functional features of the patient interface 100, primary connector 200, wye connector 300 and tri-lumen tubing 400 will be broken down into separate sections bellows.

The Tri-Lumen Tubing

FIG. 2 provides a schematic representation of the patient circuit wherein three (3) separate segments of the tri-lumen tubing 400 are used to facilitate the fluid communication between the primary connector 200 and the wye connector 300, and between the wye connector 300 and respective ones of the opposed end portions of the patient interface 100. These include a first segment 402 extending between the primary connector 200 and the wye connector 300, a second segment 404 extending between the wye connector 300 and one opposed end portion of the patient interface 100, and a third segment 406 extending between the wye connector 300 and the remaining opposed end portion of the patient interface 100.

With reference to FIG. 3, the three lumens defined by each segment 402, 404, 406 the tri-lumen tubing 400 include an air/oxygen (or high-pressure gas) delivery lumen 408, a low-pressure oxygen (or gas) delivery lumen 410, and a pressure sensing lumen 412. The tubing 400 is approximately 5.5 mm in diameter and, within the patient circuit 10, the second and third segments 404, 406 may be routed around the ears of the patient in the manner shown in FIG. 1. As will be described in more detail below, the high-pressure air/oxygen (or gas) delivery lumen 408 is for high pressure air emanating from the combination of the ventilator 12 and compressor unit 14 or for oxygen (or another gas) emanating from the ventilator 12 alone, with the low-pressure oxygen (or gas) delivery lumen 410 being for supplemental oxygen emanating from an oxygen concentrator, and the pressure sensing lumen 412 being used as a sense line between the ventilator 12 and the patient interface 100, all of these lumens 408, 410, 412 being fluidly isolated from each other.

The Patient Interface

Turning now to FIG. 5, a perspective view of an exemplary embodiment of an assembled patient interface 100 is illustrated, showing a nasal connector assembly 102, a manifold assembly 104, and a pair of jet pump assemblies 106.

In the patient interface 100, the nasal connector assembly 102 includes one or more nasal connectors 108. As used herein, the term "nasal connector(s)" may include nasal pillows or cushions, barbs, sleeves, cannulas, and other devices that deliver gas from a gas source to a patient's nose or nasal airways. For illustrative purposes only, the figures illustrate nasal pillows; however, it is understood that any reference to a nasal pillow could similarly refer to any type of nasal connector 108. The one or more nasal connectors 108 of the nasal connector assembly 102 may be directly attached to the manifold assembly 104, may fixed at a distance from the manifold assembly 104, or may be detached from the manifold assembly 104.

In the exemplary embodiment, the nasal connectors 108 used in the nasal connector assembly 102 are nasal pillows, which may impinge on a rim of the nostril, seal on the rim of the nostril, seal inside the nostril, impinge on the tissue underneath the nose, or interface with the nostril according to combinations of the above. Nasal pillows may typically be soft and compliant to allow for comfortable contact with the nostril and, if a seal is intended, compress against the nostril in a comfortable manner. Nasal pillows may typically include convolutions in the shape to allow the extension to flex in multiple planes, and to compresses along a centerline axis, to conform to the user's nose. Nasal pillows may seal against the nostril rim or other part of the nostril so that there is not inadvertent leakage between the nasal pillows and nose and so that the majority of the breathing gas flows through the nasal pillows. However, this seal does not need to be leak free, and in some embodiments, there may be a desired gas flow between the nasal pillows and the nostril. Nasal pillows may be available in different sizes so that the user can select a size that matches their anatomy. It may also be seen that these variations are equally applicable to any form of nasal connector 108 of a nasal connector assembly 102, and as such, other forms of nasal connector 108 besides nasal pillows may be customized or optimized according to the needs or desires of the user or the specific attributes of the patient interface 100.

The manifold assembly 104 may be formed of rigid, semi-rigid, or flexible/elastic materials, or may be formed of a combination of such materials, which may include a manifold assembly 104 formed having sections varying in their rigidity and softness. The external components of the manifold assembly 104, in the exemplary embodiment, together form a multi-part assembly that may include a front piece 110 and a rear piece 112 that snap together around the internal components of the manifold assembly. The manifold 104, when assembled, may have an external compound arcuate shape that is most advantageous to mate with the facial anatomy. Alternatively, the external shape manifold assembly 104 may be substantially straight, or be shaped in other configurations.

Each jet pump assembly 106 may include a jet pump housing 114 having defined therein one or more entrainment ports 116 open to ambient air. In the exemplary embodiment, each jet pump assembly 106 has a jet pump housing 114 configured with one entrainment port 116. However, it is contemplated that in other embodiments, two or more entrainment ports per jet pump assembly 106 may be utilized, such as, for example, to reduce risk of a blockage during side sleeping by a user. If a first entrainment port is blocked by the user's position during sleep, a second entrainment port may still be exposed to ambient air and may allow for proper ventilation treatment of the user. It is also contemplated that each entrainment port 116 need not constitute a single aperture, but may constitute, for example, a plurality of apertures, so long as its purpose of permitting ambient air to be entrained therethrough is accomplished.

Turning now to FIG. 6, an exploded view of the components of a patient interface 100 is illustrated, showing the internal components of the manifold assembly 104 and the internal components of the jet pump assembly 106.

As may be seen, the manifold assembly 104 may further comprise an inner tube assembly 118. The inner tube assembly 118 may be formed of a rigid, semi-rigid, malleable, or flexible material, such as, for example, silicone rubber or other similar materials, which may allow for molding of complex shapes that are not manufactural in mass with harder materials. The inner tube assembly 118 may be defined by one or more main gas flow tube portions 120, and in the exemplary embodiment, is defined by left and right gas flow tube portions 120. Each gas flow tube portion 120 defines a gas flow pathway 122 for delivering ventilation gas from the corresponding jet pump assembly 106, through the manifold assembly 104, and to the nasal connector assembly 102 wherein it may be provided to the patient. Each gas flow pathway 122 may refer to a path for gas through the inner tube assembly 118, either as one single pathway, such as from a jet pump assembly 106 to a nasal connector 108, or as multiple pathways. Each gas flow pathway 122 typically includes a flow path that is generously radiused to offer and low resistance to flow.

The inner tube assembly 118 may, in the exemplary embodiment, have the compound arcuate curve of the exterior of the manifold assembly 104. In other embodiments, however, the inner tube assembly 118 may be shaped in other ways, such as curving in other directions, such as inferiorly, or may be straight, or may be substantially malleable so as to adopt the configuration to which the remainder of the manifold assembly 104 is adjusted to. The inner tube assembly 118 may also be integral to the manifold.

The inner tube assembly 118 may be further defined by, as shown in the exemplary embodiment, one or more interconnector portions 124 between the one or more gas flow tube portions 120 defining an interconnector gas flow path 126 which places the gas flow pathways 122 defined by the gas flow tube portions 120 into fluid communication with each other. The interconnector portion 124 may function to balance pressure between the left and right nasal airways or to shut flow to the least resistive nostril. This may provide additional safety for the user in the case that one nostril is blocked. The interconnector portion 124 may also provide for a smaller and more symmetrical device.

The gas flow tube portions 120 and/or the interconnector portion 124 of the inner tube assembly 118 may include, on its outer surface, bumps or protrusions 128, which may be used to create a space between the inner tube assembly 118 and the inner walls of the external components of the manifold assembly 104, such as the front piece 110 and the rear piece 112 of the exemplary multi-piece snap-together embodiment of the manifold assembly 104. The bumps or protrusion 128, serving as spacers between the inner tube assembly 118 and the manifold assembly 104, may help promote the function of draining fluids which may accumulate between the inner tube assembly 118 and the manifold assembly 104. Such fluid may drain from the space between the inner tube assembly 118 and the inner walls of the external components of the manifold assembly 104, such as the front piece 110 and the rear piece 112 of the exemplary multi-piece snap-together embodiment of the manifold assembly 104, being removed from the manifold assembly 104 via weep holes 130 in the external components of the manifold assembly 104. In the exemplary embodiment, the weep holes 130 are positioned on the lower side of the manifold assembly 104, so as to drain downward when conventionally worn, and are formed at the junction of the snapped-together front piece 110 and the rear piece 112.

The gas flow tube portions 120 may each be configured with one or more sensing ports 132 for connection with the distal end of one or more corresponding sensing manifold tubes 134. In the exemplary embodiment, a sensing port 132 is positioned at the distal end of each gas flow tube portion 120 so as to permit fluid access to the distal end of the corresponding main gas flow pathway 122 through the sensing port 132. However, it may be seen that in other embodiments, sensing ports 132 may be positioned at other locations of the inner tube assembly 118, or at multiple locations.

Each jet pump assembly 106 may include the aforementioned jet pump housing 114 and a jet nozzle 136 for positioning inside the jet pump housing 114. Each jet pump assembly 106 may be removably or non-removably connected to a respective one of the opposed sides of the manifold assembly 104 via, for example, but without limitation, a rotational locking connection, an interference locking connection, and/or a keyed locking connection. In the exemplary embodiment illustrated in FIGS. 6 and 7, the distal ends of the front piece 110 and the rear piece 112 contain annular detents which permit the rotational attachment of the jet pump housings 114 to the manifold assembly 104. It will be recognized that through the use of a removable connection of the manifold assembly 104 to the jet pump housings 114, the manifold assembly 104 may be partially disassembled and removed from the jet pump assemblies 106, such as through the disconnection of the front piece 110 from the rear piece 112. Along these lines, it may be beneficial for the method of connecting the jet pump assemblies 106 to the manifold assembly 104 to permit rotation and/or other repositioning of the jet pump assemblies 106 relative to the manifold assembly 104.

Turning now to FIG. 7, a front view of an exemplary embodiment of the internal components of an assembled patient interface 100 is shown. Each jet nozzle 136, in the exemplary embodiment, has a proximal, upstream end and a distal, downstream end, with at least three fluidly isolated lumens therethrough. Each lumen has an opening at each of the proximal and distal ends of the jet nozzle 136. At the proximal end of each jet nozzle 136 is a high-pressure jet nozzle inlet port 138, a low-pressure jet nozzle inlet port 140, and a sensing jet nozzle inlet port 142. At the distal end of the jet nozzle 136 is a high-pressure jet nozzle outlet port 144, a low-pressure jet nozzle outlet port 146, and a sensing jet nozzle outlet port 148. The high-pressure jet nozzle outlet port 144 and the low-pressure jet nozzle outlet port 146 are configured to output into the corresponding jet pump housing 114, with the high-pressure jet nozzle outlet port 144 and the low-pressure jet nozzle outlet port 146 both being either upstream from or at least partially aligned with the entrainment port 116. As a result, the output of the respective gases from the high-pressure jet nozzle outlet port 144 and the low-pressure jet nozzle outlet port 146 achieves an entrainment effect whereby ambient air is drawn into the corresponding entrainment port 116. The outputted gases and the entrained ambient air then travels together into the corresponding gas flow pathway 122 of the manifold assembly 104 and to the nasal connector assembly 102, where it is subsequently output to the patient.

In the exemplary embodiment, the sensing jet nozzle outlet port 148 of each jet nozzle 136 is fluidly connected to a corresponding sensing manifold tube 134. Such manifold tube 134 is advanced through a corresponding lumen 135 formed within the jet pump housing 114 and extending from sensing jet nozzle outlet port 148 toward the distal end of the corresponding jet pump housing 114. As such, the lumen 135 and corresponding sensing manifold tube 134 advanced therethrough are fluidly isolated from the gases outputted from the high-pressure jet nozzle outlet port 144 and the low-pressure jet nozzle outlet port 146, and any air entrained by those gases via the entrainment port 116. The sensing manifold tube 134 travels into the manifold assembly 104, and may be generally aligned with but fluidly isolated from the corresponding gas flow pathway 122, before connecting to the sensing port 132. In the exemplary embodiment, the sensing manifold tube 134 is fully contained within the jet pump housing 114 of the corresponding jet pump assembly 106 and the manifold assembly 104, traveling outside the gas flow tube portion 120 but within the front piece 110 and rear piece 112. However, it may be seen that in other embodiments, the sensing jet nozzle outlet port 148 and the sensing tube 134 may be configured differently, such as embodiments where the sensing tube 134 travels within the corresponding gas flow pathway 122, and as such may not require the presence of a sensing port 132, but may instead sense at wherever the distal end of the sensing tube 134 is positioned.

Figure 8:
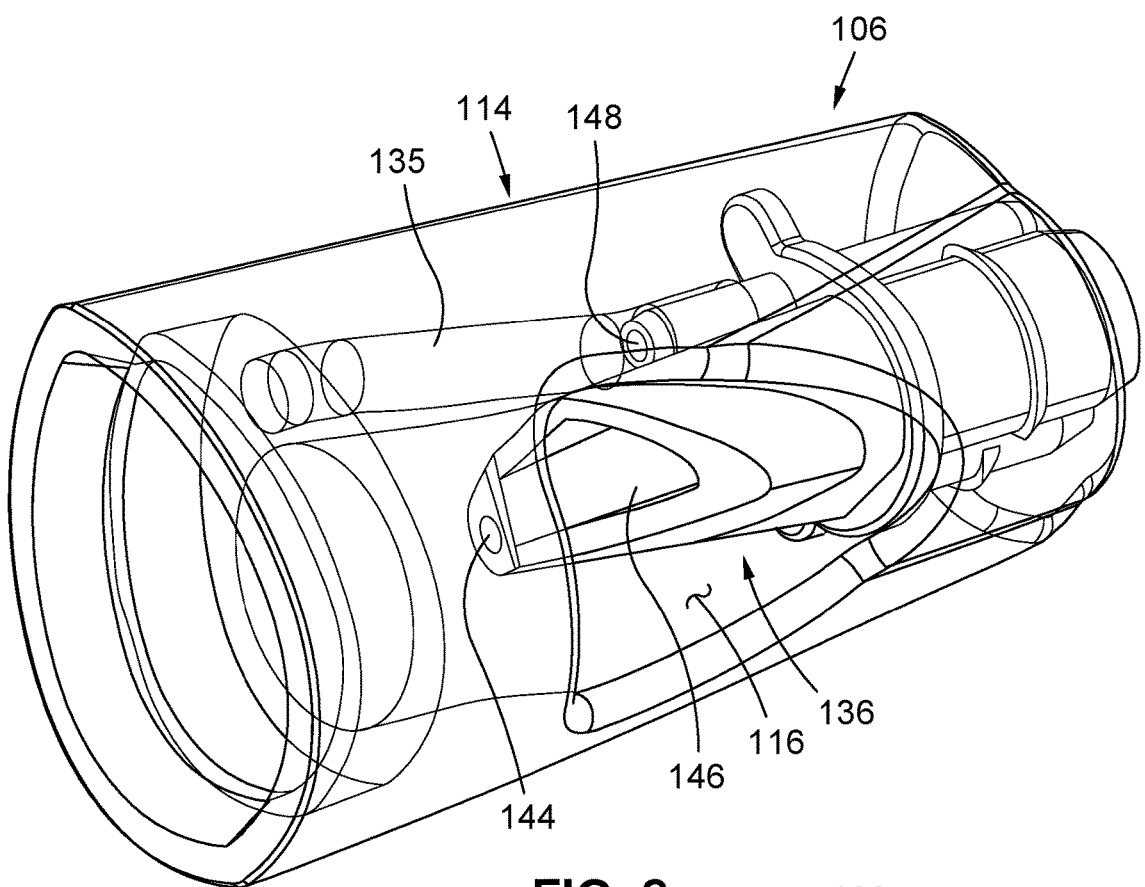
FIG. 8 is an output side perspective view of one of the two jet pump assemblies integrated into the patient interface, the housing of the assembly being shown as transparent to more clearly depict other features of the assembly.

Turning now to FIG. 8, an x-ray proximal perspective view of the internal components of a jet pump assembly 106 according to the exemplary embodiment is illustrated. In the exemplary embodiment, a substantial portion of the distal end of the jet nozzle 136 may be configured to be substantially oblique to the axial direction of the lumens passing therethrough. The low-pressure jet nozzle outlet port 146 is disposed in closer proximity to the entrainment port 116 and more rearward, while the high-pressure jet nozzle outlet port 144 is disposed at the most distal point of the jet nozzle assembly 136, further from the entrainment port 116 and forward from the low-pressure jet nozzle outlet port 146. In the exemplary embodiment, the low-pressure jet nozzle outlet port 146 is approximately crescent shaped about the lumen terminating in the high-pressure jet nozzle outlet port 144.

The aforementioned arrangement of the high and low pressure jet nozzle outlets 144, 146 relative to the entrainment port 116 may result in entrainment of ambient air in a fashion that maximizes laminar flow and minimizes turbulence of gases in the corresponding gas flow pathway 122 due to the interposition of the lower pressure gas between the high pressure gas and the entrained air serving as at least a partial buffer for shielding the high-pressure gas from the entrained air, resulting in the creation of a smoother shear force gradient across the gas flow cross section than would result without such interposition. When the gases from all three of the sources eventually blend together, they do so in a fashion that results in a more laminar fluid flow. More laminar flow of gas delivered to a patient is associated with improved user comfort and decreased noise. As may be seen, without such a shielding effect, the direct exposure of the maximum shear forces of the gas from the high-pressure jet nozzle outlet port 144 to the ambient air that is entrained through the entrainment port 116 would be more prone to generate turbulent eddy, resulting in stronger turbulence and reduced laminar flow, which is associated with reduced user comfort. Furthermore, the relatively small diameter of the high-pressure jet nozzle outlet port 144 relative to the size of the low-pressure jet nozzle outlet port 146 acts to reduce the surface area of the high-pressure gas output from the high-pressure jet nozzle outlet port 144, further reducing the likelihood of developing regions of extreme shear force disparity that lead to turbulent flow. Thus, each of the above-described Venturi-effect jet pump assemblies 106 converts and multiply high pressure/low flow breathable gas delivered by the ventilator into high flow/low pressure gas for the patient. As indicated above, the low-pressure jet nozzle outlet port 146 associated with each of the jet pump assemblies 106 is designed in a way that the positive pressure created during the delivery of the highest acceptable oxygen flow (i.e., 5 l/min) is not more than 0.5 cmH2O. As a result, and as also indicated above, such low-pressure jet nozzle outlet port 146 is effectively designed to be a very inefficient jet pump so that any delivered flow will not interfere with the proper operation of the corresponding high-pressure jet nozzle outlet port 144. This is achieved by keeping a large cross-sectional area of the low-pressure jet nozzle outlet port 146, thus having a very low flow velocity and virtually no entrainment potential.

Figure 9:
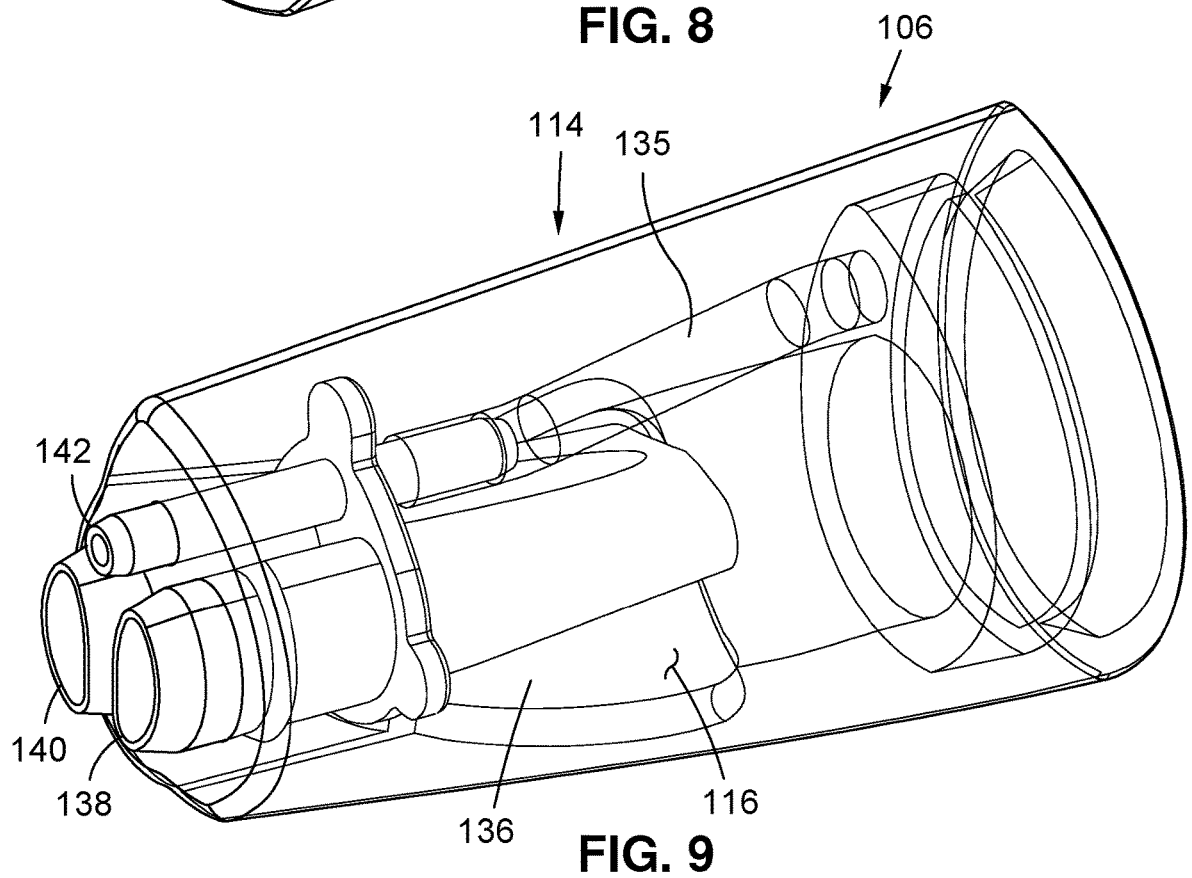
FIG. 9 is an input side perspective view of one of the two jet pump assemblies integrated into the patient housing, the housing of the assembly being shown as transparent to more clearly depict other features of the assembly.
Figure 10:
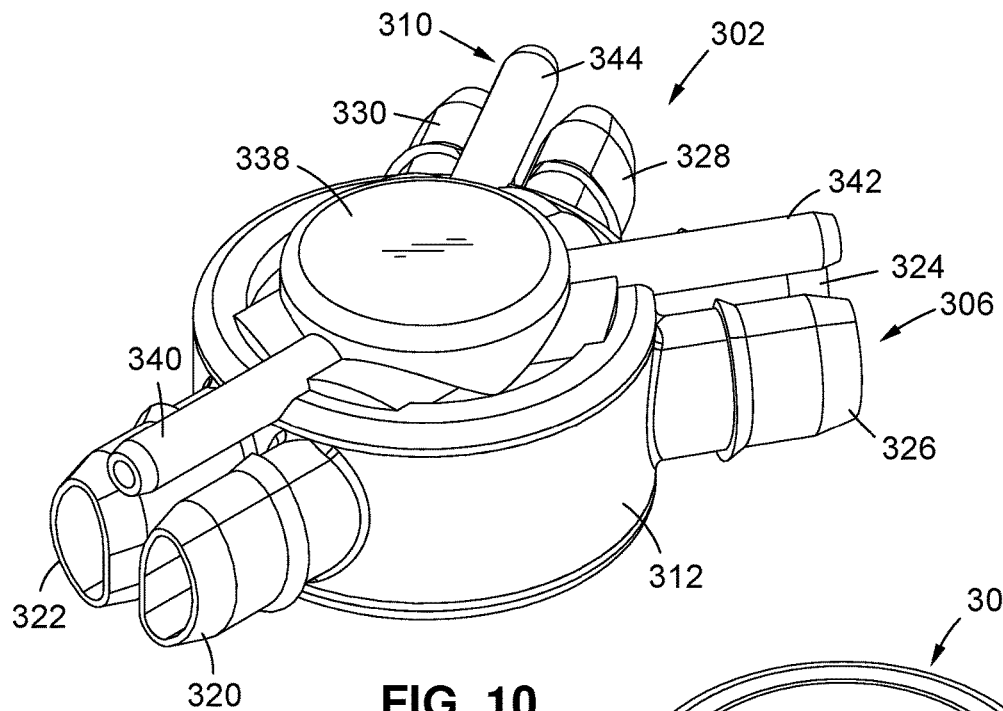
FIG. 10 is a top perspective view of the wye connector of the patient circuit.

Turning now to FIG. 9, an x-ray proximal perspective view of the internal components of a jet pump assembly 106 according to the exemplary embodiment is illustrated. The arrangement according to the exemplary embodiment of the high-pressure jet nozzle inlet port 138, the low-pressure jet nozzle inlet port 140, and the sensing jet nozzle inlet port 142 is more prominently illustrated. In the exemplary embodiment, the three inlets are male-type inlets designed to interface with a corresponding interface having three corresponding female-type ports. However, it may be seen that other arrangements of inlets or combinations of arrangements of inlet types may be appropriate, and may result in different advantages and disadvantages. It may also be seen how these jet nozzle inlets may interfaceable with a variety of connective lines by insertion of a multi-lumen line to the jet pump assembly 106 within or around the jet pump housing 114, or connection of one or more gas lines to the one or more inlets, including lines or multi-lumen lines which may not necessarily contain three of a low pressure gas, a high pressure gas, and a sensing line, so long as the corresponding portion of the jet nozzle 136 is occluded or otherwise not interfaced with. However, in an exemplary implementation of the patient circuit 10, it is contemplated that each jet pump assembly 106 will be cooperatively engaged to a corresponding one of the second and third segments 404, 406 of tri-lumen tubing 400 in manner wherein the high-pressure jet nozzle inlet port 138 is advanced into and frictionally retained with the corresponding high-pressure air/oxygen (or gas) delivery lumen 408, the low-pressure jet nozzle inlet port 140 is advanced into and frictionally retained with the corresponding low-pressure oxygen (or gas) delivery lumen 410, and the sensing jet nozzle inlet port 142 is advanced and frictionally maintained within the corresponding pressure sensing lumen 412. Glue (e.g., a UV glue) can also be used to facilitate such retention, as may barbs formed on the various ports and/or the retention force exerted by the corresponding, pre-molded jet pump housing 114.

The Primary Connector

One of the features of the patient circuit 10 is the three-way primary connector 200 that fluidly couples the patient interface 100 to the ventilator 12 and/or the compressor 14 (via the ventilator 12), and the oxygen concentrator 16 as described above. Referring now to FIGS. 14-16, additional details of the primary connector 200 will now be described. The primary connector 200 includes several constituent components, including a ventilator connector 202, an oxygen connector 204, and a housing 206. The ventilator connector 202 and the oxygen connector 204 includes various inlets and outlets that are configured to interface with corresponding ports of the ventilator 12 and the oxygen concentrator 16, and the tri-lumen tubing 400.

The ventilator connector 202 has a high-pressure conduit 208 with a high-pressure inlet port 208a and a high-pressure outlet port 208b. Additionally, there is a sense conduit 210 with a sense inlet port 210a and a sense outlet port 210b. The high-pressure conduit 208 and the sense conduit 210 are either mounted to or integral with a ventilator connector body 214. The size of the high-pressure inlet port 208a and the sense outlet port 210b, along with spatial relation between the same, are understood to correspond to those outlets of the ventilator 12 (or on the compressor unit 14 if the ventilator 12 is docked thereto). As shown, the passageway axis of the high-pressure conduit 208 and the passageway axis of the sense conduit 210 are laterally offset and parallel to each other. Along these lines, the cross-sectional shape of both the high-pressure inlet port 208a and the sense outlet port 210b are depicted as circular, though this is by way of example only and is understood to match the configuration of the outlets of the ventilator 12 or compressor unit 14.

In order to maintain a fluidly sealed connection to the ventilator 12, the high-pressure inlet port 208a and the sense outlet port 210b may each incorporate o-ring gaskets 212. The high-pressure conduit 208 and the sense conduit 210 may be fabricated from a rigid or semi-rigid material, such that the malleable or flexible materials in the corresponding interface on the ventilator 12, as well as the tri-lumen tubing 400 can be fitted thereon while maintaining a sealed relationship.

Both the high-pressure conduit 208 and the sense conduit 210 narrow at the high-pressure outlet port 208b and the sense inlet port 210a, respectively, to match the size, shape, and spatial relation between the two to correspond to those of the high-pressure gas delivery lumen 408 and the pressure sensing lumen 412 of the tubing 400, and in particular the first segment 402 thereof. The high-pressure inlet port 208a and the high-pressure outlet port 208b are understood to be coaxial, that is, the high-pressure conduit 208 has a straight body and passageway without bends. However, the sense inlet port 210a is axially offset from that of the sense outlet port 210b, reflecting the relative positional offsets between the corresponding port of the ventilator 12 and the tri-lumen tubing 400. In this regard, the sense conduit 210 defines a bend or angularly offset segment 216 that connects the sense inlet port 210a and the sense outlet port 210b. The cross-sectional shape of the high-pressure outlet port 208b generally corresponds to that of the high-pressure gas delivery lumen 408, e.g., oval-shaped. Along the same lines, the cross-sectional shape of the sense inlet port 210a likewise corresponds to that of the pressure sensing lumen 412. The primary connector 200, and in particular the high-pressure conduit 208 thereof, is contemplated to interconnect the ventilator 12 or compressor unit 14 to facilitate the delivery of high pressure air to the patient. As indicated above, in accordance with various embodiments, the compressor unit 14 may be connected to the docked ventilator 12 via a separate conduit, and the paths are combined into for introduction into the high-pressure conduit 208 of the ventilator connector 202 via corresponding outlets of the compressor unit 14. The delivery of additional oxygen is also contemplated through a low-pressure line that is separately connected to an oxygen supply, which may be an oxygen concentrator, an oxygen canister or wall connection to an oxygen gas source. In this regard, potential safety issues associated with pressurization of oxygen in a compressor, as well as flow sensor calibration with the combined delivery of oxygen and air may be avoided.

As briefly noted above, the primary connector 200 includes the oxygen connector 204 through which supplemental oxygen may be delivered to the patient interface 100. The oxygen connector 204 is generally defined by u-shaped low-pressure conduit 218, with a low-pressure inlet port 218a on one end and a low-pressure outlet port 218b on an opposed end. In an exemplary configuration, the opening of the low-pressure inlet port 218a faces in the opposite direction as the opening of the high-pressure inlet port 208a and the sense inlet port 210a, so that a connection to an external oxygen source may be made. There is a first bend 220, which is illustrated as perpendicular corner. There is lateral extension 222, followed by another perpendicular second bend 224 that leads to the low-pressure outlet port 218b. According to some implementations, the lateral extension 222 is open, and so there may be a plug 223 that cover such open segment.

Like the high-pressure outlet port 208b, the low-pressure outlet port 218b is sized and configured to interface with the corresponding lumen of the tri-lumen tubing 400, e.g., the low-pressure gas delivery lumen 410. As such, the low-pressure outlet port 218b is understood to have an oval cross section. Again, the tri-lumen tubing 400 is understood to be constructed of a semi-rigid or flexible material that forms a sealing relationship with the low-pressure outlet port 218b. As a further means to ensure this sealing relationship, the low-pressure outlet port 218b includes a barb 213.

The oxygen connector 204, and specifically the dimensions of the lateral extension 222, is understood to be configured for low pressure outlet port 218b to be positioned in prescribed offset relationships to the high-pressure outlet port 208b and the sense inlet port 210a. These offset relationships are understood to correspond to those of the low pressure gas delivery lumen 410 to the high pressure gas delivery lumen 408 and the pressure sensing lumen 412, such that the tri-lumen tubing 400 is attached to the ventilator connector 202 and the oxygen connector 204, with each of the conduits thereof being in fluid communication with the respective lumens of the tri-lumen tubing 400, e.g., the high pressure gas delivery lumen 408, the pressure sensing lumen 412 and the low pressure gas delivery lumen 410. The ventilator connector 202 is understood to be mounted to the oxygen connector 204, and thus there may be a support platform 226 as well as a support strut 228 for positioning the ventilator connector 202 relative to the oxygen connector 204. The pseudo-hexagonal feature on the platform 226 may be used as a plug to close the sense line.

The ventilator connector 202 and the oxygen connector 204 are disposed within the housing 206. The housing 206 thus defines a first opening 230a from which the high-pressure inlet port 208a extends, and a second opening 230b from which the sense outlet port 210b extends. According to various embodiments, the housing 206 may be fabricated from a semi-rigid or malleable material that flexibly retains the ventilator connector 202 and the oxygen connector 204 within. To minimize lateral movement of the ventilator connector 202 during insertion and removal, and to provide a keyed plug that allows for visual and tactile insertion into the corresponding socket of the ventilator 12, there may also be a connector clip 232. As shown, the connector clip 232 is defined by a square end 234 and an opposed tapered end 236. The connector clip 232 may include support frame 238 that retains the ventilator connector body 214. The housing 206 is further defined by a tubing receiver extension 240. The tri-lumen tubing 400 is received by the housing 206, and specifically via the tubing receiver extension 240 that is opposite the openings 230 for the connection to the ventilator 12 or compressor unit 14. More particularly, the tubing receiver extension 240 includes an integral flexible grommet 242 that is contemplated to relieve the stresses imparted to the connection between the tri-lumen tubing 400, on one end, and the ventilator connector 202 and the oxygen connector 204, on the other.

The Wye Connector

The wye connector 300 comprises two main components, i.e., an interior housing 302 and an over-molded exterior housing 304. The interior housing 302 resides within the exterior housing 304, the primary purpose of which is to provide a more streamlined, aesthetically pleasing form factor for the wye connector 300.

The interior housing 302 comprises a main body 306, a low-pressure plug plate 308 attached to one side of the main body 306, and a sensing plate 310 also attached to the main body 306 in opposed relation to the plug plate 308. The main body 306 comprises an annular, circularly configured outer wall 312. While the outer wall 312 defines an opposed pair of distal rims, it does not define a continuous path or opening between such distal rims. Rather, the main body 306 also includes a separator wall 314 which spans or extends completely diametrically across the interior area defined by the outer wall 312, thus effectively segregating such interior area into a first, top section 316 and a second, bottom section 318 as viewed from the perspective shown in FIGS. 12 and 13. As will be described in more detail below, when the plug and sensing plates 308, 310 are each attached to the main body 306, and in particular to respective ones of the opposed rims defined by the outer wall 312 thereof, the plug plate 308 effectively encloses the bottom section 318. This enclosed bottom section 318 collectively defined by the outer wall 312, separator wall 314 and plug plate 308 defines a low-pressure chamber of the wye connector 300. Similarly, the sensing plate 310 effectively encloses the top section 316, with this enclosed top section 316 collectively defined by the outer wall 312, separator wall 314 and sensing plate 310 defining a sensing chamber of the wye connector 300.

Protruding from the exterior surface of the outer wall 312 of the main body 306 is a high-pressure inlet port 320 and a low-pressure inlet port 322 which are disposed in side-by-side relation to each other, and each have a generally kidney bean shaped cross-sectional profile. Also protruding from the exterior surface of the outer wall 312 of the main body 306 is a first high-pressure outlet port 324 and a first low-pressure outlet port 322 which are disposed in side-by-side relation to each other, and identically configured to the high and low-pressure inlet ports 120, 122. Further protruding from the exterior surface of the outer wall 312 of the main body 306 is a second high-pressure outlet port 328 and a second low-pressure outlet port 330 which are also disposed in side-by-side relation to each other, and identically configured to the high and low-pressure inlet ports 320, 322. When viewed from the perspective shown in FIG. 11, the arrangement of the various high and low-pressure ports is such that if the high and low-pressure inlet ports 320, 322 are viewed as being in the 6 o'clock position on the main body 306, the first high and low-pressure outlet ports 324, 326 are in the 11 o'clock position, with the second high and low-pressure outlet ports 324, 326 being in the 1 o'clock position.

Figure 11:
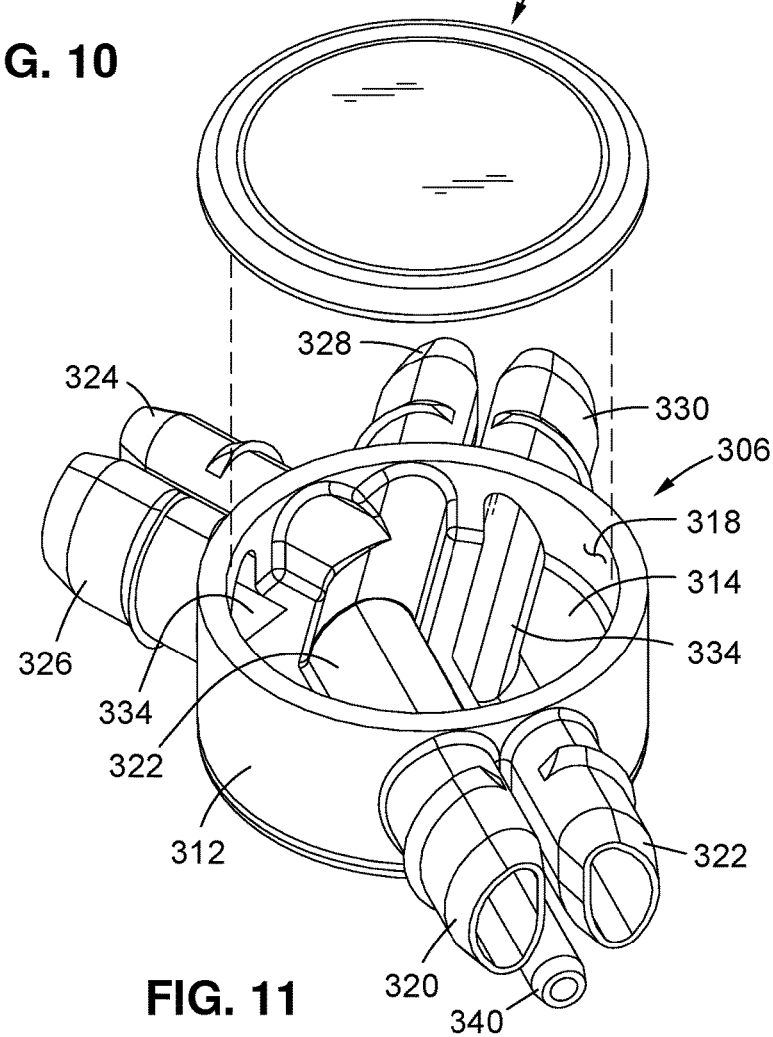
FIG. 11 is a bottom exploded view of the wye connector shown in FIG. 10 taken from a first perspective.
Figure 12:
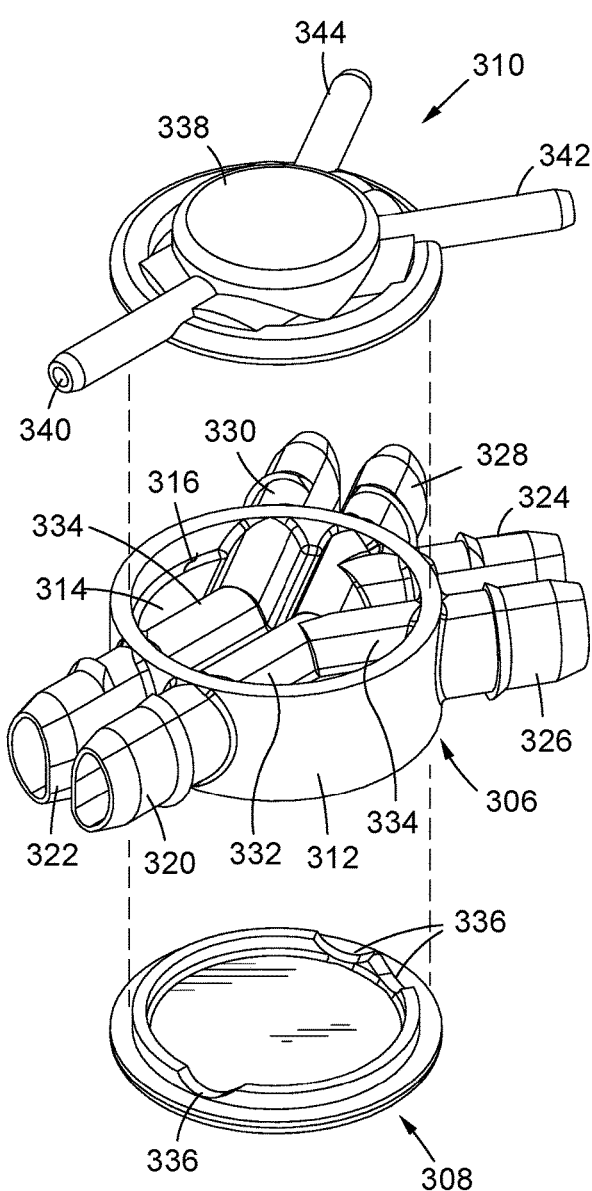
FIG. 12 is a top exploded view of the wye connector shown in FIG. 10.
Figure 13:
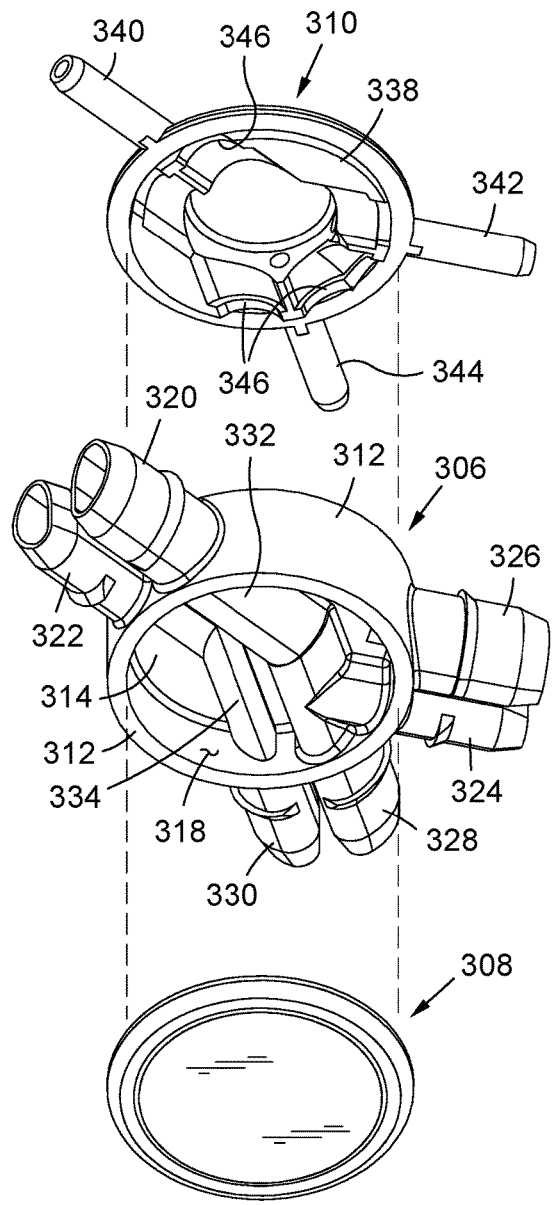
FIG. 13 is bottom exploded view of the wye connector shown in FIG. 10 taken from a second perspective.

As seen in FIGS. 11-13, the main body 306 is configured such that the high-pressure inlet port 320 is in direct fluid communication with each of the first and second high pressure outlet ports 324, 328. Such fluid communication is facilitated by an enclosed, tunnel like channel 332 which is an integral portion of the separator wall 314, with portions of the channel 332 thus protruding into each of the low-pressure and sensing chambers, though being fluidly isolated therefrom. As seen in FIGS. 11-13, a portion of the channel 332 has a generally Y-shaped configuration as allows it to effectively bifurcate flow from the high-pressure inlet port 320 into each of the first and second high-pressure outlet ports 324, 328.

As seen in FIGS. 11 and 13, the main body 306 is also configured such that the low-pressure inlet port 322 is in direct fluid communication with low-pressure chamber defined by the enclosed bottom section 318. In a similar fashion, each of the first and second low-pressure outlet ports 326, 330 is also in direct fluid communication with low-pressure chamber defined by the enclosed bottom section 318. As such, low-pressure gas entering the low-pressure chamber via the low-pressure inlet port 322 is effectively routed into each of the first and second low-pressure outlet ports 326, 330, but is fluidly isolated from the channel 332 and hence the first and second high-pressure outlet ports 324, 328. To assist is promoting flow into the low-pressure chamber from the low-pressure inlet port 322 and from the low-pressure chamber into each of the first and second low-pressure outlet ports 326, 330, it is contemplated that the underside of the separator wall 314 partially defining the low-pressure chamber may be formed to include integral grooves 334 which each have a generally semi-circular cross-sectional profile, and thus protrude into the sensing chamber, though being fluidly isolated therefrom. The grooves 334 are sized and shaped to provide an effective increase in the cross-sectional area of open communication between each of the low-pressure ports 322, 326, 330 and the low-pressure chamber.

As indicated above, in the wye connector 300, the attachment of the plug plate 308 to the corresponding rim of the main body 306 effectively encloses the bottom section 118, thus facilitating the formation of the low-pressure chamber. Along these lines, as seen in FIG. 12, the plug plate 308 is formed to include three (3) semi-circular recesses 336 about its periphery. When the plug plate 308 is attached to the main body 306, these recesses 336 are positioned to accommodate corresponding portions of the bifurcated channel 332 protruding into the low-pressure chamber.

As also indicated above, in the wye connector 300, the attachment of the sensing plate 310 to the corresponding rim of the main body 306 effectively encloses the top section 316, thus facilitating the formation of the sensing chamber. The sensing plate 310 includes a circularly configured body 338. Protruding from the body 338 is a sensing inlet port 340 which has a generally circular cross-sectional profile. Also protruding from the body 340 is a first sensing outlet port 342 and a second sensing outlet port 344 which are each identically configured to the sensing inlet port 340. When viewed from the perspective shown in FIG. 12, the arrangement of the various sensing ports is such that if the sensing inlet port 340 is viewed as being in the 6 o'clock position on the body 338, the first sensing outlet port 342 is in the 1 o'clock position, with the second sensing outlet port 344 being in the 11 o'clock position. The wye connector 300 is configured such that the sensing inlet and outlet ports 340, 342, 344 are each in direct fluid communication with sensing chamber defined by the enclosed top section 316, yet are fluidly isolated from the channel 332 (and hence the high-pressure inlet and outlet ports 320, 324, 328) as well as the low-pressure chamber (and hence the low-pressure inlet and outlet ports 322, 326, 330). As such, open fluid communication between the sensing inlet and outlet ports 340, 342, 344 is facilitated by the intervening sensing chamber. As seen in FIG. 13, the body 338 of the sensing plate 310 is formed to include six (6) semi-circular recesses 346 about its periphery. When the sensing plate 310 is attached to the main body 306, these recesses 346 are positioned to accommodate corresponding portions of the bifurcated channel 332 and grooves 334 protruding into the sensing chamber.

In an exemplary implementation of the patient circuit 10, it is contemplated that the wye connector 300 will be cooperatively engaged to each of the first, second and third segments 402, 404, 406 of tri-lumen tubing 400. In greater detail, the high and low-pressure inlet ports 320, 322 and the sensing inlet port 340 are advanced into and frictionally retained with corresponding ones of the high-pressure air/oxygen (or gas) delivery lumen 408, the low-pressure oxygen (or gas) delivery lumen 410, and the pressure sensing lumen 412 of the first tubing segment 402. Similarly, the first high and low-pressure outlet ports 324, 326 and the first sensing outlet port 342 are advanced into and frictionally retained with corresponding ones of the high-pressure air/oxygen (or gas) delivery lumen 408, the low-pressure oxygen (or gas) delivery lumen 410, and the pressure sensing lumen 412 of the second tubing segment 404, with the second high and low-pressure outlet ports 328, 330 and the second sensing outlet port 344 being advanced into and frictionally retained with corresponding ones of the high-pressure air/oxygen (or gas) delivery lumen 408, the low-pressure oxygen (or gas) delivery lumen 410, and the pressure sensing lumen 412 of the third tubing segment 406.

Patient Circuit Modes of Use

As indicated above, the patient circuit 10 of the present disclosure is capable of accommodating multiple configurations of the ventilation system. In a first of these configurations, the patient interface 100 (and hence the patient wearing the same) is placed into fluid communication with high-pressure air emanating from the ventilator 12 directly or from the ventilator 12 via the compressor unit 14 (if the ventilator 12 is docked in the compressor unit). In this arrangement, the primary connector 200 is connected to the ventilator 12 or compressor unit 14 such that high-pressure air is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. In this arrangement, an unobstructed pressure sensing path is also defined between the ventilator 12 and the patient interface 100 by, in sequence, the sense conduit 210 of the ventilator connector 202, the pressure sensing lumen 412 of the first tubing segment 402, the sensing inlet port 340 and the first and second sensing outlet ports 342, 344 of the wye connector 300, the pressure sensing lumens 412 of the second and third tubing segments 404, 406, the sensing lumens defining the above-described sensing jet nozzle inlet and outlets 142, 148 in the jet nozzles 136 of the jet pump assemblies 106, the sensing manifold tubes 134, and the sensing ports 132.

In a second of these configurations, the patient interface 100 is placed into fluid communication with high-pressure air emanating from the ventilator 12 directly or from the ventilator 12 via the compressor unit 14 (if the ventilator 12 is docked in the compressor unit), but also with supplemental low-pressure oxygen supplied from the oxygen concentrator 16 and bypassing the compressor unit 14 and ventilator 12. The high-pressure air delivery sequence is the same as described above for the first configuration. Oxygen from the oxygen concentrator 16 is provided to the patient in a flow path comprising, in sequence, the oxygen connector 204 of the primary connector 200, the low-pressure oxygen (or gas) delivery lumen 410 of the first tubing segment 402, the low-pressure inlet and outlet ports 322, 326, 330 of the wye connector 300, the low-pressure air/oxygen (or gas) delivery lumens 410 of the second and third tubing segments 404, 406, and the low-pressure gas delivery lumens defining the above-described low-pressure jet nozzle inlet and outlet ports 140, 146 in the jet nozzles 136 of the jet pump assemblies 106. In this arrangement, an unobstructed pressure sensing path is also defined between the ventilator 12 and the patient interface 100 in the same sequence as described above for the first configuration.

In a third of these configurations, the patient interface 100 is placed into fluid communication with oxygen emanating from a canister or wall connection via the ventilator 12 (with the compressor unit 14 being removed from the ventilation system) and further with oxygen emanating from an oxygen concentrator 16, the patient being ventilated with oxygen and also receiving additional oxygen from the concentrator 16. In this arrangement, the primary connector 200 is connected to the ventilator 12 such that oxygen from the canister or wall connection is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. Oxygen from the oxygen concentrator 16 is provided to the patient in a flow path comprising the same sequence as described above for the second configuration. An unobstructed pressure sensing path is also defined between the ventilator 12 and the patient interface 100 in the same sequence as described above for the first configuration.

In a fourth of these configurations, the patient interface 100 is placed into fluid communication with oxygen emanating from a canister or wall connection via the ventilator 12 (with the compressor unit 14 and the oxygen concentrator 16 being removed from the ventilation system). In this arrangement, the primary connector 200 is connected to the ventilator 12 such that oxygen from the canister or wall connection is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. An unobstructed pressure sensing path is also defined between the ventilator 12 and the patient interface 100 in the same sequence as described above for the first configuration.

In a fifth of these configurations, the patient interface 100 is placed into fluid communication with oxygen emanating from a canister or wall connection via the ventilator 12 (with the compressor unit 14 and the oxygen concentrator 16 being removed from the ventilation system), with the low-pressure oxygen port of the primary connector 200 of the patient circuit 10 being connected to the low pressure port of the regulator used with the canister to allow the patient to be ventilated with oxygen while also receiving additional oxygen from the same gas source, i.e., the canister. In this arrangement, oxygen from the canister or wall connection is provided to the patient in a flow path comprising the same sequence as described above for the fourth configuration. Additional oxygen from the same source is provided to the patient in a flow path comprising, in sequence, the oxygen connector 204 of the primary connector 200, the low-pressure oxygen (or gas) delivery lumen 410 of the first tubing segment 402, the low-pressure inlet and outlet ports 322, 326, 330 of the wye connector 300, the low-pressure air/oxygen (or gas) delivery lumens 410 of the second and third tubing segments 404, 406, and the low-pressure gas delivery lumens defining the above-described low-pressure jet nozzle inlet and outlet ports 140, 146 in the jet nozzles 136 of the jet pump assemblies 106. In this arrangement, an unobstructed pressure sensing path is also defined between the ventilator 12 and the patient interface 100 in the same sequence as described above for the first configuration.

Alternative Arrangements

Figure 17:
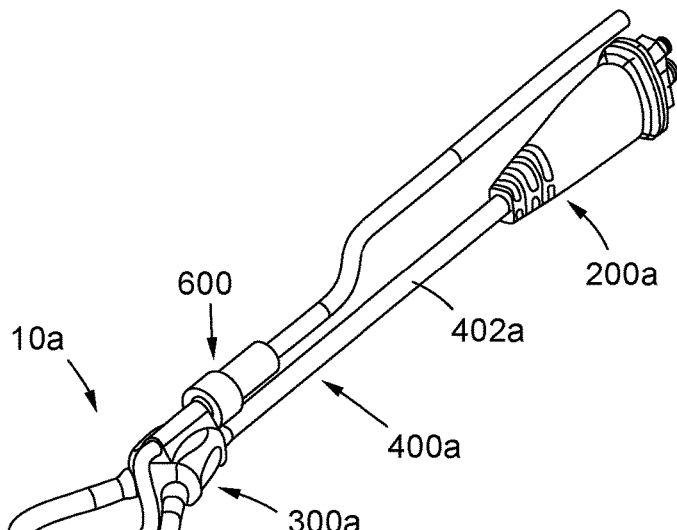
FIG. 17 is a top perspective view of an alternative embodiment of the patient circuit.
Figure 18:
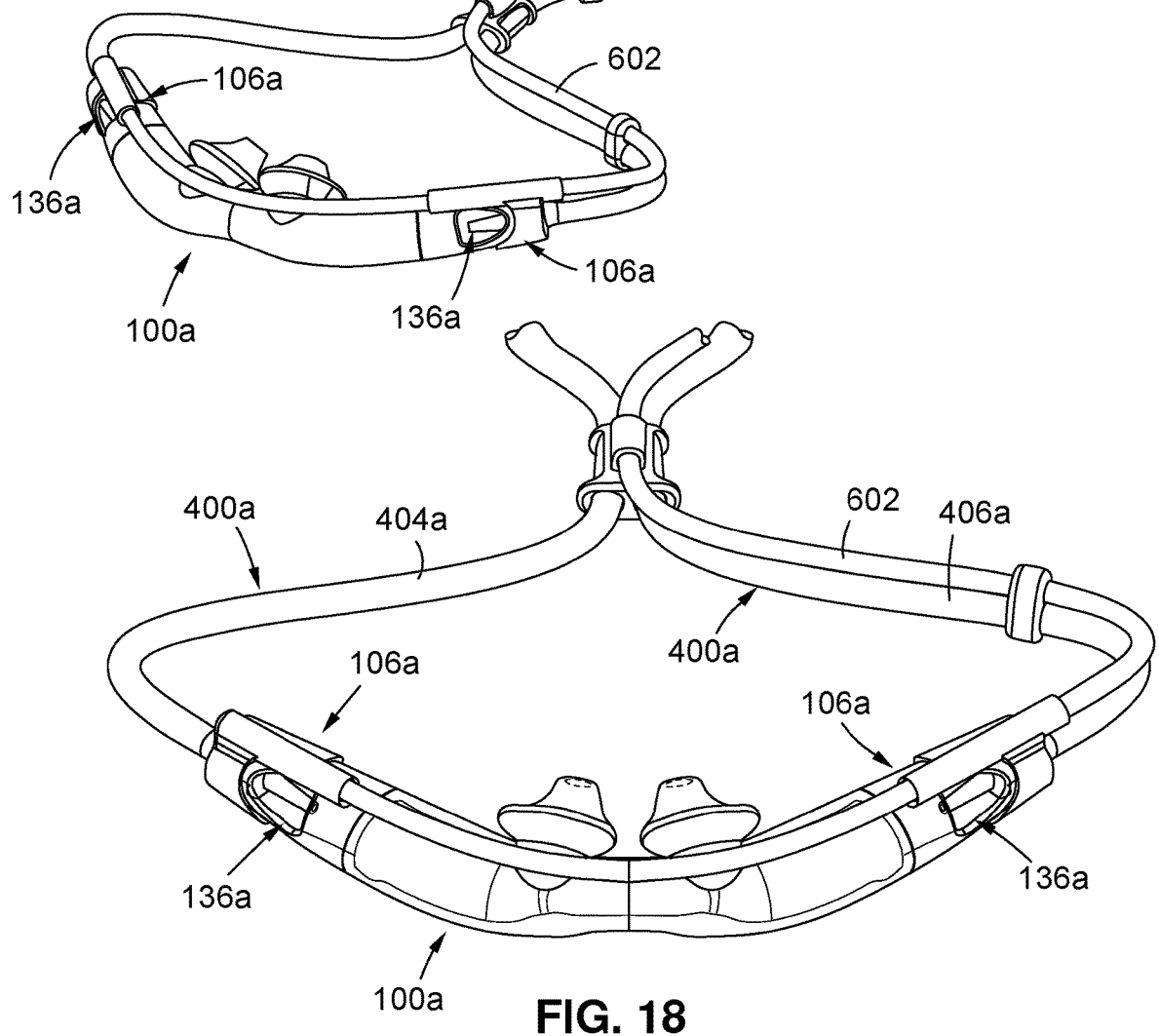
FIG. 18 is a front perspective view of the alternative patient circuit shown in FIG. 17.

As indicated above, and with reference to FIGS. 17 and 18, in one possible alternative embodiment, the patient circuit 10a is provided with an oxygen connector 600, compatible with 6 mm oxygen cannula connectors, that can be glued or clipped over the wye connector 300a of the patient circuit 10a. The wye connector 300a differs from the wye connector 300 through the elimination of the above-described low-pressure inlet and outlet ports 322, 326, 330. In a similar vein, in the patient circuit 10a, the primary connector 200a differs from the primary connector 200 through the elimination of the above-described oxygen connector 204, with a first segment 402a of bi-lumen tubing 400a replacing the first segment 402 of tri-lumen tubing 400, as only two lumens are needed to effectuate high pressure gas delivery and pressure sensing fluid communication between the primary connector 200a and wye connector 300a in the patient circuit 10a.

From the oxygen connector 600, a single tube 602 can deliver oxygen to one or a pair of delivery nozzles that can be glued or clipped in place over or around one entrainment area or respective ones of the entrainment areas of the jet pump assembles 106a included in the patient interface 10a. In other words, the tube 602 (e.g., oxygen line) may deliver gas to one delivery nozzle, and be extended to deliver the gas to another delivery nozzle located on the other side of the patient interface 10a, which is clipped or glued in place near or over the other entrainment area. Because the oxygen delivery nozzles are connected in series, this arrangement requires that the holes of the nozzles and the cross section of the tube 602 be balanced in a way to ensure the same amount of oxygen flow is delivered by both nozzles. Along these lines, in the jet pump assemblies 106a of the patient interface 100a integrated into the patient circuit 10a, the jet nozzles 136a differ from the jet nozzles 136 of the jet pump assemblies 106 by virtue of the elimination of the low-pressure gas delivery lumen defining the above-described low-pressure jet nozzle inlet and outlet 140, 146. With this the elimination of the low-pressure gas delivery lumens in the jet nozzles 136a of the jet pump assemblies 106a, in the patient circuit 10a, second and third segments 404a, 406a of bi-lumen tubing 400a replace the second and third segments 404, 406 of tri-lumen tubing 400, as only two lumens within each segment 404, 406a are needed to effectuate high pressure gas delivery and pressure sensing fluid communication between the wye connector 300a and the patient interface 100a.

A further alternative arrangement is to have the two nozzles connected in parallel, so that two tubes depart from the oxygen connector 600 secured on the wye connector 300a of the patient interface 10a. This configuration is easier to pneumatically balance, though having additional tubing over both the first and second bi-lumen tubing segments 404a, 406a used to facilitate high pressure air/oxygen delivery and pressure sensing in the patient circuit 10a. The clip-on or glue-on nozzles are designed in a way to minimize the occlusion of the entrainment ports, so that the inspiratory and expiratory resistance values of the patient interface 10a can be retained unaltered. The delivery nozzles are also positioned in a way such that the oxygen flow is delivered in the zone between the nozzle and the throat of each of the jet pump assembles 106a. This position is considered optimal to minimize any positive pressure created by the oxygen flow and to maximize the amount of oxygen that is entrained and delivered to the patient. Clips and a modified cinch can also be included in the design to help manage the tube 602 and tubing segments 404a, 406a around the patients' face. The small portion of the tube 602 connecting the left and right oxygen nozzles in the series configuration is designed in a way that its presence does not interfere with the pillows of the patient interface 100a.

This disclosure provides exemplary embodiments of the present disclosure. The scope of the present disclosure is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A system for providing ventilation to an individual, the system comprising:
    a ventilator;
    an oxygen concentrator;
    a manifold housing defining at least one gas pathway; and
    a patient circuit connecting the ventilator and the oxygen concentrator to the at least one gas pathway of the manifold housing, the patient circuit comprising:
        one or more segments of tubing, each of the one or more segments of tubing defining a high-pressure gas lumen, a low-pressure gas lumen, and a pressure sensing lumen that are isolated from each other within the tubing;
        a jet pump housing coupled to the manifold housing and defining at least one entrainment port in fluid communication with ambient air;
        a jet nozzle cooperatively engaged to the jet pump housing, the jet nozzle defining a high-pressure jet nozzle outlet port in fluid communication with the high-pressure gas lumen of each of the one or more segments of tubing and a low-pressure jet nozzle outlet port in fluid communication with the low-pressure gas lumen of each of the one or more segments of tubing, the high-pressure jet nozzle outlet port being disposed forward from the low-pressure jet nozzle outlet port, at least the high-pressure jet nozzle outlet port being operative to facilitate air entrainment through the entrainment port and mixing of the entrained air with gas concurrently introduced into the gas pathway from the high and low-pressure jet nozzle outlet ports; and at least one sensing tube in fluid communication with the pressure sensing lumen of each of the one or more segments of tubing and extending into fluid communication with the gas pathway at a position distal to the high-pressure jet nozzle outlet port and the low-pressure jet nozzle outlet port.

2. The system of claim 1, wherein the jet nozzle includes a sensing jet nozzle outlet port in fluid communication with the pressure sensing lumen of each of the one or more segments of tubing, the at least one sensing tube being fluidly connected to the sensing jet nozzle outlet port.

3. The system of claim 1, wherein a compliant tube is disposed within the manifold housing for forming the gas pathway through the manifold housing.

4. The system of claim 3, wherein the at least one sensing tube travels within the manifold housing and outside the compliant tube before extending into fluid communication with the gas pathway.

5. The system of claim 3, wherein the at least one sensing tube enters into fluid communication with the gas pathway via a pressure sensing port of the compliant tube.

6. The system of claim 3, wherein the gas pathway of the compliant tube is devoid of corners and abrupt bends and angles.

7. The system of claim 3, wherein one or more nasal connectors are fluidly coupled to the gas pathway in the compliant tube.

8. The system of claim 7, wherein the one or more nasal connectors are one or more nasal pillows.

9. The system of claim 7, wherein the at least one sensing tube comprises a pair of sensing tubes fluidly coupled to the gas pathway proximate respective ones of the nasal connectors.

10. The system of claim 3, wherein the compliant tube further comprises one or more bumps to create space between the compliant tube and an inner surface of the manifold housing.

11. The system of claim 1, wherein the high-pressure jet nozzle outlet port and the low-pressure jet nozzle outlet port are each at least partially aligned with the entrainment port.

12. The system of claim 1, wherein the low-pressure jet nozzle outlet port is disposed in closer proximity to the entrainment port in comparison to the high-pressure jet nozzle outlet port.

13. The system of claim 1, wherein the jet nozzle is formed such that the low-pressure jet nozzle outlet port is oblique relative to a flow axis of gas emanating therefrom.

14. The system of claim 1, wherein a pair of jet pump housings are coupled to the manifold housing in opposed relation to each other.

15. The system of claim 1, wherein the manifold housing is a multi-piece manifold housing.

16. The system of claim 1, wherein one or more nasal connectors are coupled to the manifold housing.

17. The system of claim 1, wherein the gas pathway is divided into a left gas pathway and a right gas pathway, and further comprising an interconnecting channel between the left gas pathway and the right gas pathway.

18. A system for providing ventilation to an individual, the system comprising:
a ventilator;
a manifold housing defining at least one gas pathway; and
a patient circuit connecting the ventilator to the at least one gas pathway of the manifold housing, the patient circuit comprising:
one or more segments of tubing, each of the one or more segments of tubing defining a high-pressure gas lumen, a low-pressure gas lumen, and a pressure sensing lumen that are isolated from each other within the tubing;
a jet pump housing coupled to the manifold housing and defining at least one entrainment port in fluid communication with ambient air;
a jet nozzle cooperatively engaged to the jet pump housing, the jet nozzle defining a high-pressure jet nozzle outlet port in fluid communication with the high-pressure gas lumen of each of the one or more segments of tubing and a low-pressure jet nozzle outlet port in fluid communication with the low-pressure gas lumen of each of the one or more segments of tubing, the high-pressure jet nozzle outlet port being disposed forward from the low-pressure jet nozzle outlet port, at least the high-pressure jet nozzle outlet port being operative to facilitate air entrainment through the entrainment port and mixing of the entrained air with gas concurrently introduced into the gas pathway from the high and low-pressure jet nozzle outlet ports; and
at least one sensing tube in fluid communication with the pressure sensing lumen of each of the one or more segments of tubing and extending into fluid communication with the gas pathway at a position distal to the high-pressure jet nozzle outlet port and the low-pressure jet nozzle outlet port.

19. The system of claim 18 wherein the patient circuit further connects an oxygen source to the at least one gas pathway of the manifold housing.

20. A system for providing ventilation to an individual, the system comprising:
a manifold housing defining at least one gas pathway; and
a patient circuit for connecting a ventilator to the at least one gas pathway of the manifold housing, the patient circuit comprising:
one or more segments of tubing, each of the one or more segments of tubing defining a high-pressure gas lumen, a low-pressure gas lumen, and a pressure sensing lumen that are isolated from each other within the tubing;
a jet pump housing coupled to the manifold housing and defining at least one entrainment port in fluid communication with ambient air;
a jet nozzle cooperatively engaged to the jet pump housing, the jet nozzle defining a high-pressure jet nozzle outlet port in fluid communication with the high-pressure gas lumen of each of the one or more segments of tubing and a low-pressure jet nozzle outlet port in fluid communication with the low-pressure gas lumen of each of the one or more segments of tubing, the high-pressure jet nozzle outlet port being disposed forward from the low-pressure jet nozzle outlet port, at least the high-pressure jet nozzle outlet port being operative to facilitate air entrainment through the entrainment port and mixing of the entrained air with gas concurrently introduced into the gas pathway from the high and low-pressure jet nozzle outlet ports; and
at least one sensing tube in fluid communication with the pressure sensing lumen of each of the one or more segments of tubing and extending into fluid communication with the gas pathway at a position distal to the high-pressure jet nozzle outlet port and the low-pressure jet nozzle outlet port.

* * * * *